United States Patent
Fu

(10) Patent No.: US 12,331,071 B2
(45) Date of Patent: Jun. 17, 2025

(54) BILE ACID DERIVATIVE SALT, CRYSTAL STRUCTURE THEREOF, PREPARATION METHOD THEREFOR AND USE THEREOF

(71) Applicant: XI'AN BIOCARE PHARMA LTD., Xi'an (CN)

(72) Inventor: Guoqin Fu, Xi'an (CN)

(73) Assignee: XI'AN BIOCARE PHARMA LTD., Xi'An (CN)

( * ) Notice: Subject to any disclaimer, the term of this patent is extended or adjusted under 35 U.S.C. 154(b) by 472 days.

(21) Appl. No.: 17/779,979

(22) PCT Filed: Apr. 7, 2021

(86) PCT No.: PCT/CN2021/085785
§ 371 (c)(1),
(2) Date: May 25, 2022

(87) PCT Pub. No.: WO2021/204142
PCT Pub. Date: Oct. 14, 2021

(65) Prior Publication Data
US 2023/0054001 A1     Feb. 23, 2023

(30) Foreign Application Priority Data

Apr. 8, 2020   (CN) .......................... 202010272501.0

(51) Int. Cl.
*C07J 43/00*         (2006.01)
(52) U.S. Cl.
CPC .......... *C07J 43/003* (2013.01); *C07B 2200/13* (2013.01)
(58) Field of Classification Search
CPC ..................... C07J 43/003; C07B 2200/13
See application file for complete search history.

(56) References Cited

U.S. PATENT DOCUMENTS

| | | | |
|---|---|---|---|
| 2016/0185815 A1 | 6/2016 | Wang et al. | |
| 2020/0131212 A1* | 4/2020 | Fu ........................ | A61K 31/685 |

FOREIGN PATENT DOCUMENTS

| | | |
|---|---|---|
| CN | 104672290 | 6/2015 |
| CN | 109929005 | 6/2019 |
| KR | 20170087935 A | 7/2017 |
| WO | WO2016045480 | 3/2016 |
| WO | WO2016086115 | 6/2016 |
| WO | WO2016173524 | 11/2016 |
| WO | WO2019119832 | 6/2019 |

OTHER PUBLICATIONS

Ashizawa, K., *Chemistry of Polymorphism and Crystallization of Pharmaceuticals*, (2002): 273; 278; 305-317.
First Office Action issued in Chinese Patent Application No. 202180006768.8, mailed May 20, 2023.
First Office Action issued in Japanese Patent Application No. 2022-530836, mailed May 9, 2023.
Hirayama, N., *Organic Compound Crystal Preparation Handbook*, (2008): 17-23; 37-40; 45-51; 57-65.
"Pharmaceutics," *Department of Pharmacy, Second Military Medical University of Chinese People's Liberation Army*, 1 (1981): 8 pages.
Balbach, S. et al., "Pharmaceutical evaluation of early development candidates "The mg approach"," *International Journal of Pharmaceutics*, 275 (2004): 1-12.
Caira, M. R., "Crystalline Polymorphism of Organic Compounds," *Topics in Current Chemistry*, 198 (1998): 164-208.
Office Action issued in Australian Patent Application No. 2021251935, dated Feb. 13, 2023.
Singhal, D. et al., "Drug polymorphism and dosage form design: a practical perspective," *Advanced Drug Delivery Reviews*, 56 (2004): 335-347.
English translation of International Search Report issued in International Patent Application No. PCT/CN2021/085785, dated Jul. 5, 2021.
English Translation of an Office Action issued in Korean Patent Application No. 10-2022-7018193, dated Jun. 27, 2024.

\* cited by examiner

*Primary Examiner* — Timothy R Rozof
(74) *Attorney, Agent, or Firm* — Parker Highlander PLLC

(57) ABSTRACT

The present invention provides a salt of a bile acid derivative, a crystal form thereof, a preparation method therefor and use thereof. The salt of a bile acid derivative, the crystal form thereof and a composition thereof provided by the present invention can improve cholestasis, reduce portal pressure, and improve liver function, and can be used for preparing medicaments for treating or alleviating chronic liver diseases, metabolic diseases, portal hypertension and related diseases.

20 Claims, 5 Drawing Sheets

BILE ACID DERIVATIVE SALT, CRYSTAL STRUCTURE THEREOF, PREPARATION METHOD THEREFOR AND USE THEREOF

This application is a national phase application under 35 U.S.C. § 371 of International Application No. PCT/CN2021/085785, filed Apr. 7, 2021, which claims the benefit of Chinese Patent Application No. 202010272501.0, filed Apr. 8, 2020, the entire contents of which are hereby incorporated by reference.

FIELD

The present disclosure relates to the field of medicinal chemistry, and specifically relates to a salt of a bile acid derivative, crystalline form structure thereof, preparation method and application thereof.

BACKGROUND

Bile acids have a variety of physiological functions. They not only play an important role in the absorption, transport and distribution of fats and fat-soluble vitamins, but also act as signaling molecules to activate nuclear receptors and then regulate the metabolism of bile acids and cholesterol. Enterohepatic circulation of bile acids is an important regulatory mechanism regulating the rate of bile acid synthesis. Bile acids are synthesized from the liver into the gallbladder, secreted into the small intestine, reabsorbed in the ileum and transported back to the liver through the portal circulation.

Cholestasis mainly occurs in mid-and late pregnancy, or patients with liver fibrosis, hepatic sclerosis or bile duct obstruction, and shows clinical manifestations, such as itching, choleplania, elevated serum alkaline phosphatase (ALP). For cholestasis, ursodesoxycholic acid (UDCA) is currently the most commonly used drug, which is a steroid compound, an analog of cholic acid, having a choleretic effect. UDCA is used to treat cholesterol stones or prevent the formation of drug-induced stones, but it has a poor agonistic effect on the bile acid nuclear receptor FXR, so it has limitations in the treatment of cholestasism. Some patients with cholestasis are not sensitive to UDCA.

Studies have shown that the FXR receptor (farnesoid X receptor) is a member of the hormone nuclear receptor superfamily. FXR is a bile acid sensor. Several research groups reported that bile acids are FXR endogenous ligands under physiological conditions, evidenced by the finding that bile acids can not only bind directly to FXR, but also lead to the recruitment of synergistic activating factors and co-repressors through their interaction, which indicated that bile acids are endogenous FXR ligands, so FXR is also known as bile acid receptors. As a bile acid receptor, FXR can maintain the homeostasis of bile acids by regulating the expression of genes involved in bile acid metabolism. FXR is a key regulator of cholesterol homeostasis, triglyceride synthesis, and lipogenesis (Crawley, Expert Opinion Ther. Patents (2010), 20(8): 1047-1057). FXR-related diseases include treatment of liver disease, diabetes, vitamin D-related diseases, side effects caused by drugs, and hepatitis.

The applicant of the present application filed an application (CN201810930184.X) on Aug. 15, 2018 disclosing bile acid derivative compounds for the treatment of metabolic diseases. These compounds can significantly relieve cholestasis and accelerate biliary excretion, so they have a therapeutic effect on bile excretion disorders related diseases.

Moreover, they can correspondingly reduce values of ALT, AST, ALP, and have a certain effect on repairing liver damage. In addition, these compounds can reduce portal pressure and have a therapeutic effect on portal hypertension, and also have excellent pharmacodynamic activity as can be seen from the contents of the description. These compounds, however, may not be heated or ground due to their low melting points, causing much difficulties of formulation research. Moreover, they are not easy to be stored and weighed due to their poor solubility, causing inconvenience to the later development.

Therefore, it is of great significance to provide these compounds in a solid form with better druggability upon the premise of ensuring their efficacy.

SUMMARY

In view of that, the technical problem to be solved by the present disclosure is to provide a salt of a bile acid derivative, crystalline form structure thereof, their preparation method and application. The salt of the bile acid derivative provided by the present disclosure not only has good solubility and stability, but also have good efficacy.

Compared with the existing technology, the present disclosure provides a salt of a bile acid derivative, crystalline form structure thereof, their preparation method and application. The salt of a bile acid derivative in the present disclosure is obtained by reacting a compound having structure of Formula (I) with an acid. Through experiments, it is found in the present disclosure that reacting the compound having structure of Formula (I) with a specific acid allows the produced salt to have good solubility and stability, and also have FXR receptor agonist activity. The salt can relieve cholestasis, reduce portal pressure, improve liver functions, and be used to manufacture medicaments for treating or relieving chronic liver diseases, metabolic diseases or portal hypertension and related diseases thereof.

DETAILED DESCRIPTION

Figure 1:
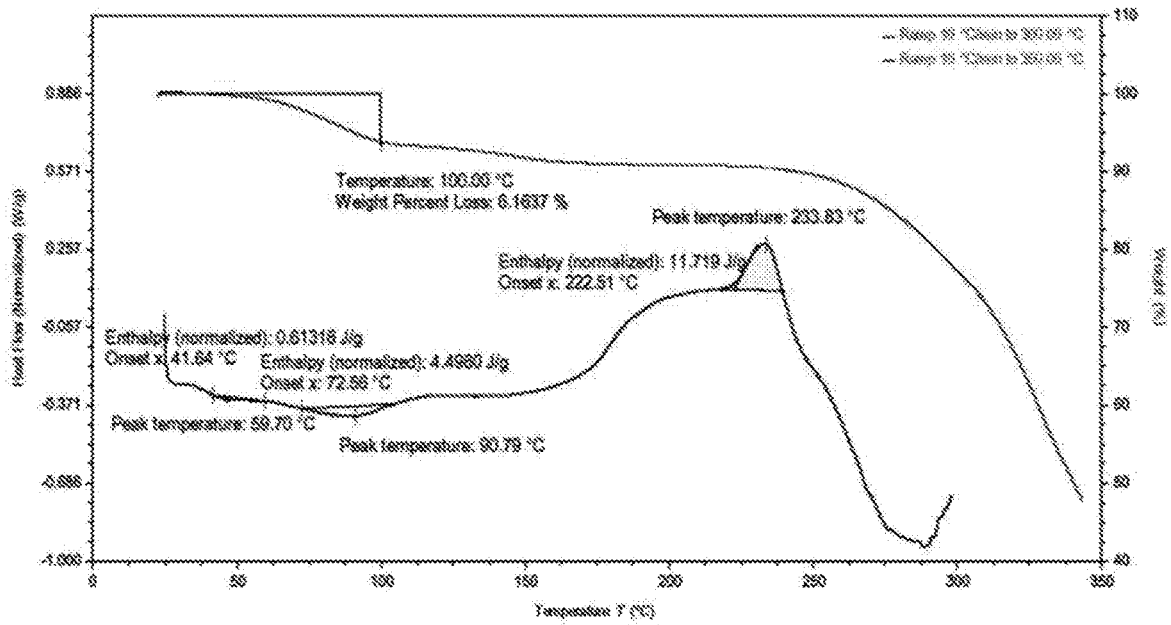
FIG. 1 shows differential scanning calorimetry (DSC) and thermogravimetric analysis (TGA) curves of Compound 1 prepared in Example 1.

The present disclosure provides a salt of a bile acid derivative, produced by reacting a compound having structure of Formula (I) with an acid,

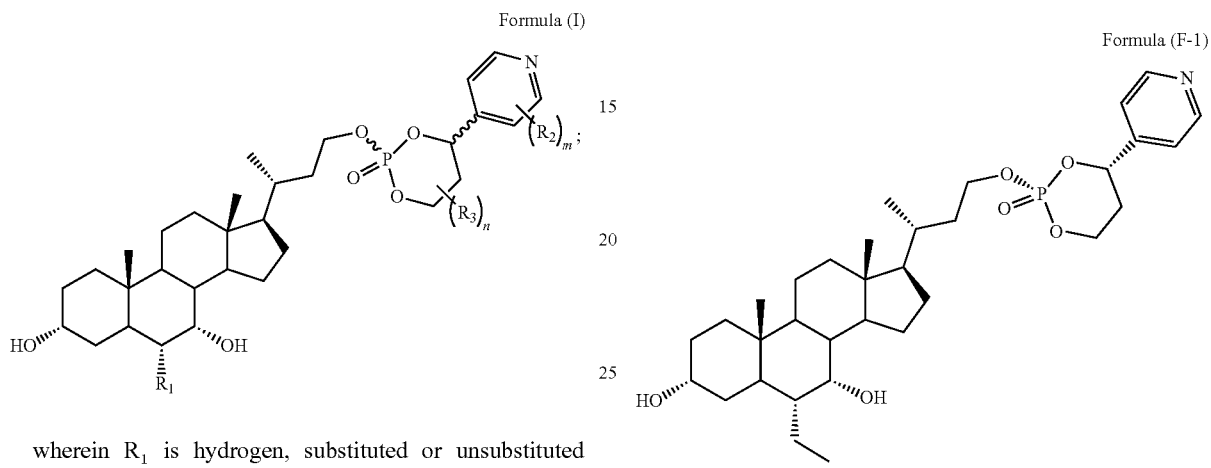

Formula (I)

wherein $R_1$ is hydrogen, substituted or unsubstituted $C_1$-$C_{12}$ alkyl or halogen;
each $R_2$ is independently any one or more selected from substituted or unsubstituted $C_1$-$C_{12}$ alkyl, halogen, cyano, hydroxyl, nitro, a sulfo group, and carboxyl;
m is 0, 1, 2, 3 or 4;
each $R_3$ is independently one or more selected from substituted or unsubstituted $C_1$-$C_{12}$ alkyl, halogen, hydroxyl, $C_6$-$C_{30}$ aryl;
n is 0, 1, 2, 3, 4 or 5;
the acid is an inorganic acid or an organic acid;
the inorganic acid is selected from hydrochloric acid;
wherein ⌇ in the structural formula represents that the three-dimensional configuration of the compound can be above or below the paper,
the organic acid is selected from methanesulfonic acid, oxalic acid, p-toluenesulfonic acid, L-tartaric acid, fumaric acid or maleic acid, and preferably selected from methanesulfonic acid and p-toluenesulfonic acid.

In some embodiments of the present disclosure, the $R_1$ is hydrogen, substituted or unsubstituted $C_2$-$C_6$ alkyl or halogen, and preferably hydrogen, fluorine, chlorine, bromine, methyl, ethyl, n-propyl, isopropyl, n-butyl, isobutyl, tert-butyl, n-pentyl, isoamyl or n-hexyl.

each $R_2$ is independently any one or more selected from substituted or unsubstituted $C_2$-$C_6$ alkyl, halogen, cyano, hydroxyl, nitro, a sulfo group and carboxyl. In some embodiments, each $R_2$ is independently selected from fluorine, chlorine, bromine, methyl, ethyl, n-propyl, isopropyl, n-butyl, isobutyl, tert-butyl, n-pentyl, isoamyl, n-hexyl, hydroxyl, nitro, a sulfo group and carboxyl.

each $R_3$ is independently one or more selected from substituted or unsubstituted $C_2$-$C_6$ alkyl, halogen, hydroxyl, $C_6$-$C_{18}$ aryl. In some embodiments, each $R_3$ is independently selected from fluorine, chlorine, bromine, methyl, ethyl, n-propyl, isopropyl, n-butyl, isobutyl, tert-butyl, n-pentyl, isoamyl, n-hexyl, hydroxyl, phenyl, naphthyl, anthracenyl or phenanthryl.

Specifically, the compound represented by Formula (I) is (F-1), Formula (F-2), Formula (F-3), Formula (F-4), Formula (F-5), Formula (F-6), Formula (F-7), Formula (F-8), (F-9), Formula (F-10), Formula (F-11), Formula (F-12), (F-13), Formula (F-14), Formula (F-15), Formula (F-16), (F-17), Formula (F-18), Formula (F-19), Formula (F-20), (F-21), Formula (F-22), Formula (F-23), Formula (F-24), (F-25), Formula (F-26), Formula (F-27), Formula (F-28), (F-29), Formula (F-30), Formula (F-31) or Formula (F-32),

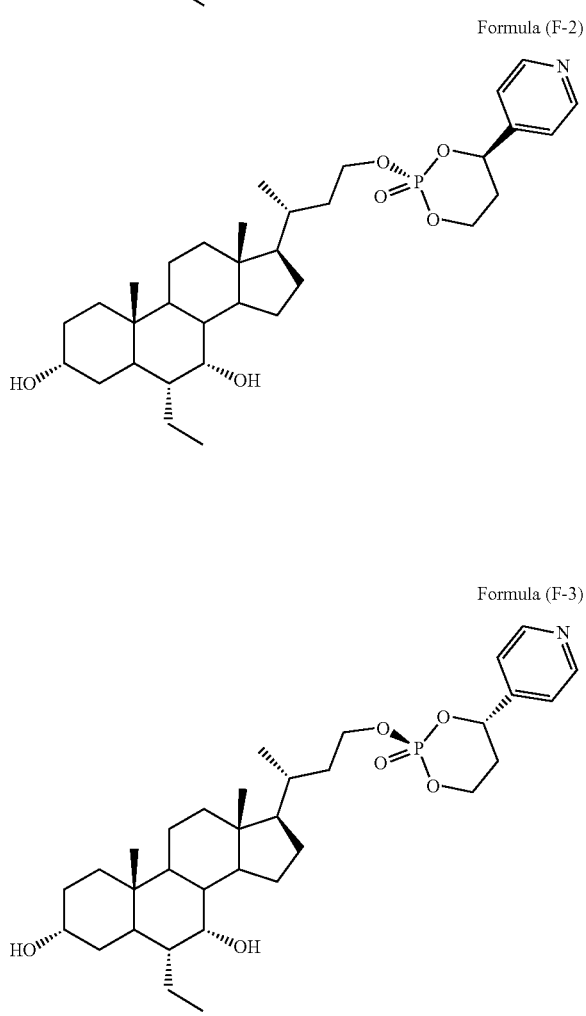

Formula (F-1)

Formula (F-2)

Formula (F-3)

Formula (F-4)
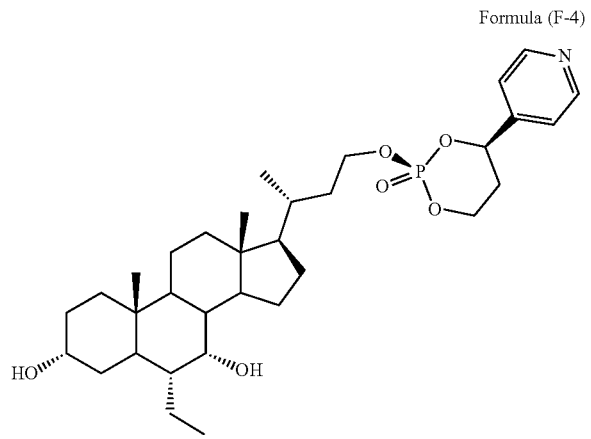
Formula (F-5)
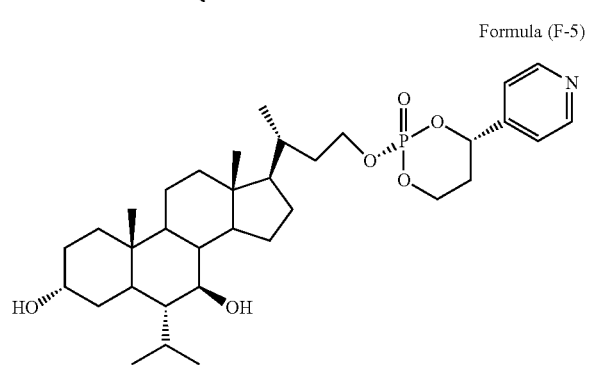
Formula (F-6)
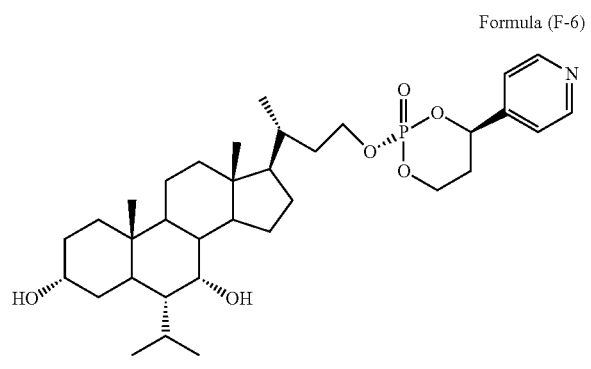
Formula (F-7)
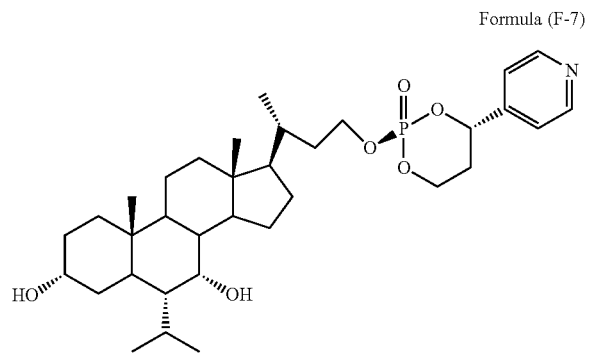
Formula (F-8)
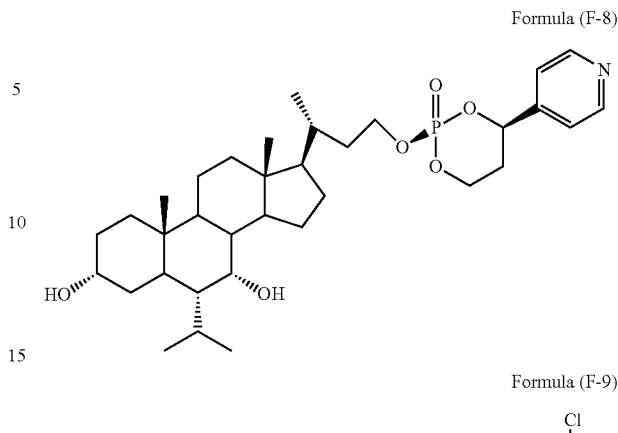
Formula (F-9)
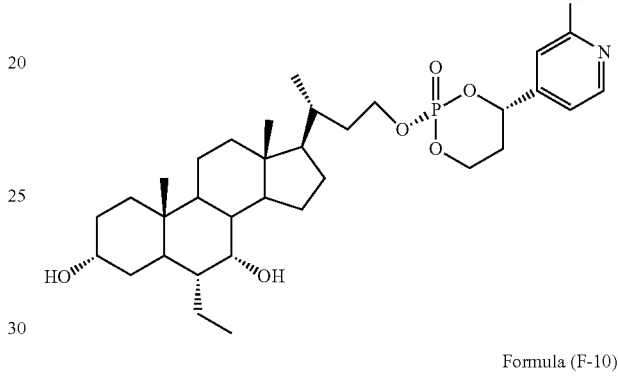
Formula (F-10)
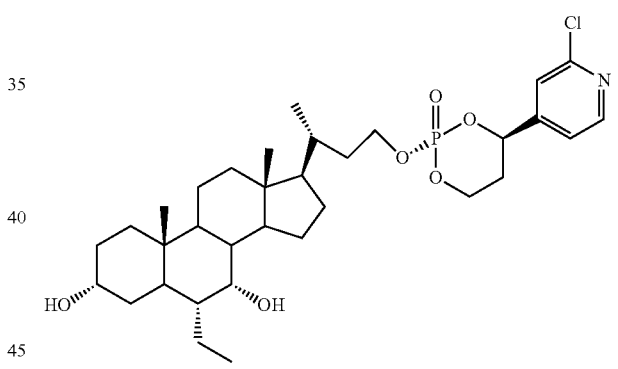
Formula (F-11)
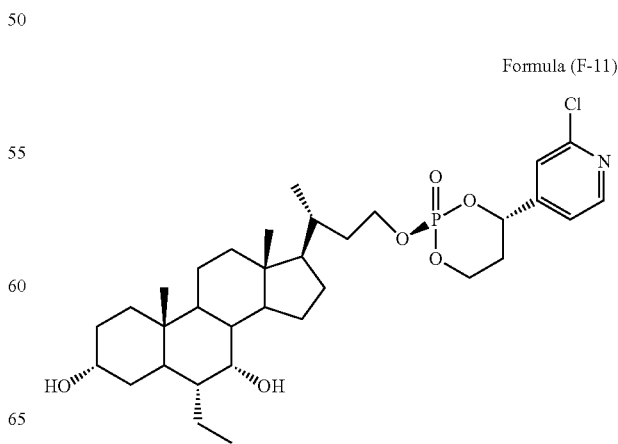

Formula (F-12)
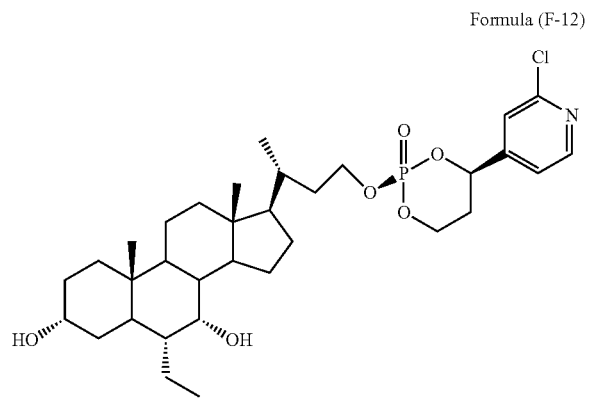
Formula (F-16)
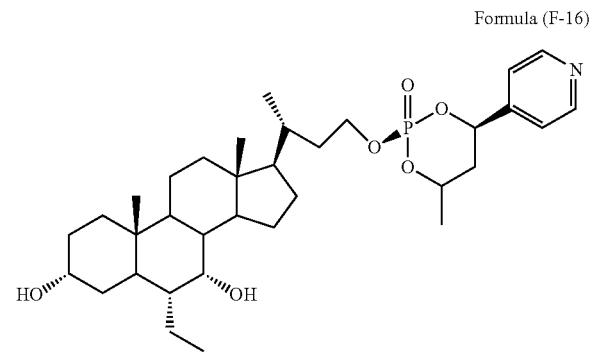
Formula (F-13)
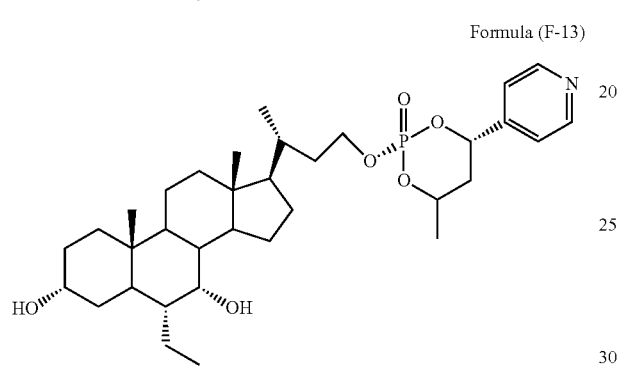
Formula (F-17)
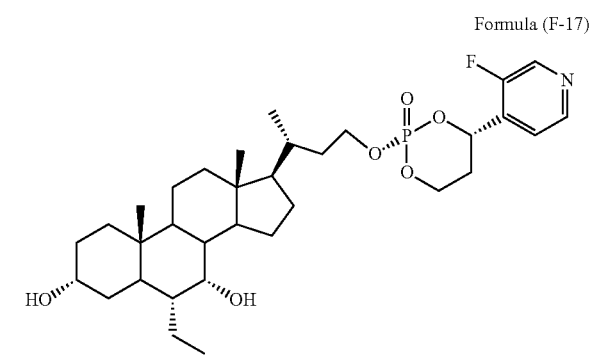
Formula (F-14)
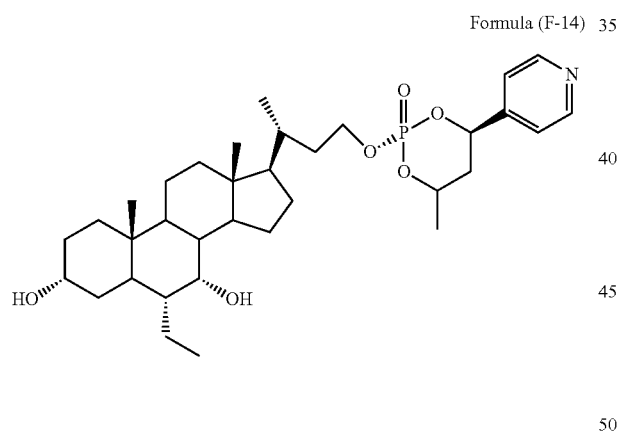
Formula (F-18)
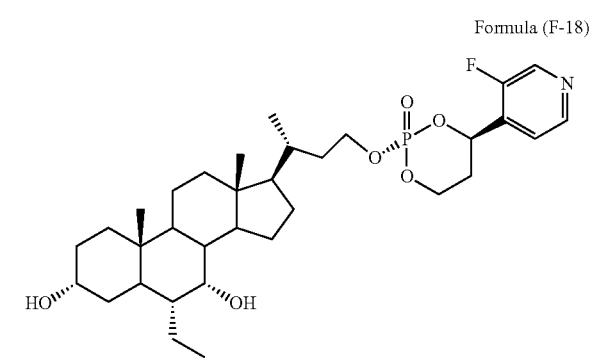
Formula (F-15)
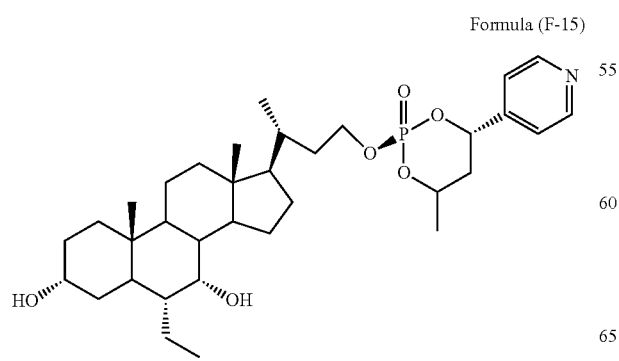
Formula (F-19)
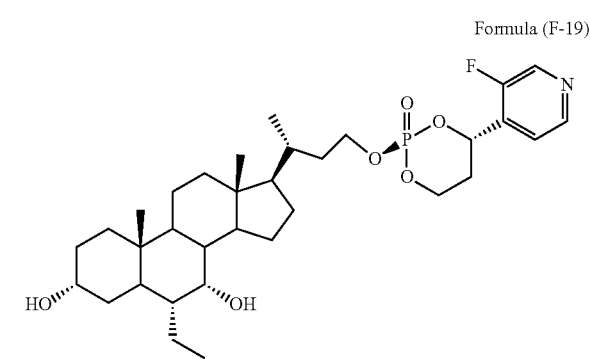

Formula (F-20)

Formula (F-21)

Formula (F-22)

Formula (F-23)

Formula (F-24)

Formula (F-25)

Formula (F-26)

Formula (F-27)

Formula (F-28)

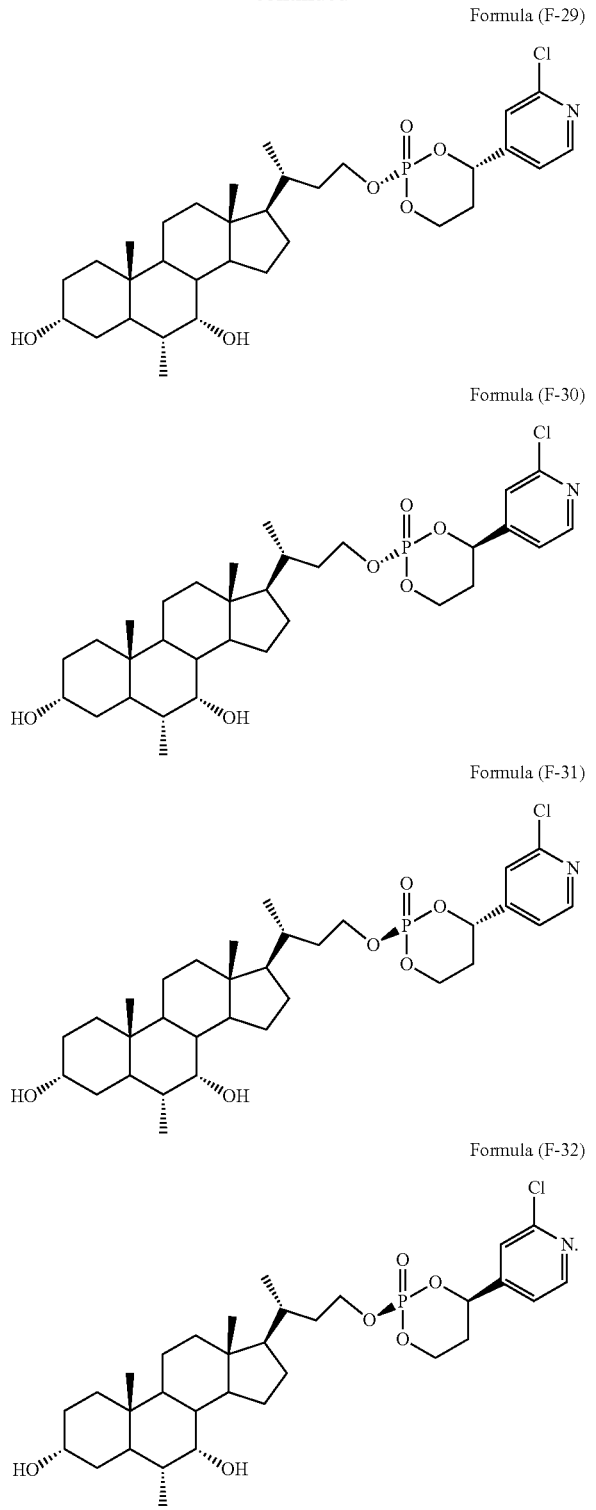

Formula (F-29)

Formula (F-30)

Formula (F-31)

Formula (F-32)

More specifically, the salt of the bile acid derivative is a hydrochloride salt, mesylate salt, oxalate salt, p-toluenesulfonate salt, L-tartrate salt, fumarate salt or maleate salt of the compound of Formula (F-1), Formula (F-2), Formula (F-3), Formula (F-4), Formula (F-5), Formula (F-6), Formula (F-7), Formula (F-8), (F-9), Formula (F-10), Formula (F-11), Formula (F-12), (F-13), Formula (F-14), Formula (F-15), Formula (F-16), (F-17), Formula (F-18), Formula (F-19), Formula (F-20), (F-21), Formula (F-22), Formula (F-23), Formula (F-24), (F-25), Formula (F-26), Formula (F-27), Formula (F-28), (F-29), Formula (F-30), Formula (F-31) or Formula (F-32).

In the present disclosure, combination of the compound having structure of Formula (I) with a suitable salt via ionic bonds or covalent bonds can change the charge distribution in the molecule and adjust the physicochemical properties of the compound. It was found in experiments that the salts of the compound provided by the present disclosure have sample preparing process conducive to process amplification, better physical properties than that in a free base state, improved melting point, improved solubility, high purity, and significantly improved stability over the free base compounds.

The present disclosure further provides a method for preparing a salt of a bile acid derivative comprising:
  mixing and reacting a compound represented by Formula (I), a first solvent and an acid, to obtain the salt of the bile acid derivative;
  the acid is an inorganic acid or an organic acid;
  the inorganic acid is selected from hydrochloric acid; the organic acid is selected from methanesulfonic acid, oxalic acid, p-toluenesulfonic acid, L-tartaric acid, fumaric acid and maleic acid, and preferably from methanesulfonic acid and p-toluenesulfonic acid;
  the first solvent is one or more of methanol, ethanol, isopropanol, isobutanol, 2-butanone, tetrahydrofuran, dichloromethane, acetonitrile, methyl tert-butyl ether, acetone, ethyl acetate, methyl formate, isopropyl acetate or n-hexane.

In accordance with the present disclosure, a compound represented by Formula (I), a first solvent and an acid are mixed and reacted to produce the bile acid derivative salt. The molar ratio of the compound represented by Formula (I) and hydrogen ion in the acid is 1: (0.9-1.5) and more preferably 1: (1.0-1.2). In some embodiments, the first solvent is one or more of methanol, ethanol, isopropanol, isobutanol and dichloromethane. In the present disclosure, in order to promote the reaction, the preparation is preferably carried out by:

(1) dissolving the compound represented by Formula (I) into the first solvent;
(2) to the resulting solution, adding the acid, well-mixing and performing the reaction, to obtain a reaction solution;
(3) to the reaction solution obtained in step (2), adding a second solvent, and mixing to precipitate a solid, or concentrating to produce a solid, or cooling to precipitate a solid;

wherein the first solvent is one or more of methanol, ethanol, isopropanol, isobutanol and dichloromethane; the second solvent is at least one or more of ethyl acetate, acetonitrile, dichloromethane, methyl tert-butyl ether, acetone, methyl formate, isopropyl acetate and tetrahydrofuran; the second solvent has a different polarity from the first solvent; and the volume ratio of the first solvent to the second solvent is 1:(1-7). More specifically, the combination of the volume ratio of the first solvent to the second solvent is: methanol:dichloromethane=1:(1-5), methanol:ethyl acetate=1: (2-6), methanol:acetonitrile=1:(1-2), methanol:ethyl acetate:acetonitrile=1:3:1, isopropanol:dichloromethane:ethyl acetate=1:1:6, isopropanol:ethyl acetate=1: (2-6), methanol:acetonitrile:methyl formate=1:1:4, ethanol:ethyl acetate=1: (2-6), ethanol:dichloromethane:ethyl acetate=1:1:6, isopropanol:methyl tert-butyl ether=1: (1-6), or methanol:methyl tert-butyl ether=1:(1-6).

More specifically, the volume ratio of the first solvent to the second solvent is methanol:dichloromethane=1: (3-4), methanol:ethyl acetate=1: (3-4), methanol:acetonitrile=1: (1-2), methanol:ethyl acetate:acetonitrile=1:3:1, isopropanol:dichloromethane:ethyl acetate=1:1:6, isopropanol:ethyl acetate=1: (2-4), methanol:acetonitrile:methyl formate=1:1:4, ethanol:ethyl acetate=1: (3-4), ethanol:dichloromethane:ethyl acetate=1:1:6, isopropanol:methyl tert-butyl ether=1:(2-4) or methanol:methyl tert-butyl ether=1:(2-6).

In the method of preparing the acid addition salt of the compound represented by Formula (I), in the step (1), the solution obtained from dissolving the compound represented by Formula (I) in the first solvent has a concentration of 0.2 g/mL-2 g/mL.

In order to promote the dissolution of the compound represented by Formula (I) in the first solvent, stirring or ultrasonication can be employed, and the dissolution can be performed at a temperature of 15-50° C. In some more specific embodiments, in step (1), the dissolution of the compound represented by Formula (I) in the first solvent can be carried out at a temperature of 15-20° C. or 20-45° C.

The present disclosure further provides a crystalline form of a salt of a bile acid derivative represented by Formula (S-1), named as crystalline form A,

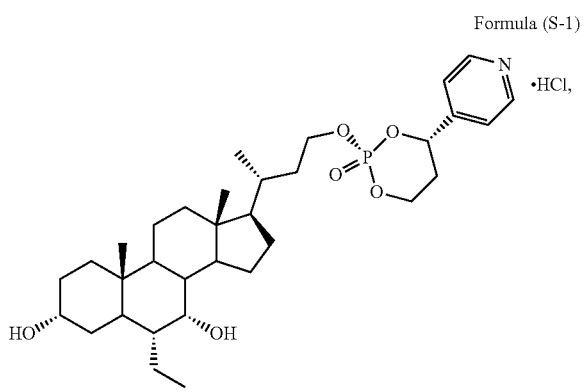

Formula (S-1)

wherein the crystalline form A exhibits an X-ray powder diffraction spectrum comprising diffraction peaks at 2θangles of 9.58°±0.2°, 13.79°±0.2°, 16.81°±0.2°, 19.19°±0.2°. More specifically, the crystalline form A exhibits an X-ray powder diffraction spectrum comprising diffraction peaks at 2θangles of 6.68°±0.2°, 9.58°±0.2°, 11.37°±0.2°, 13.30°±0.2°, 13.79°±0.2°, 16.81°±0.2° and 19.19°±0.2°. Furthermore specifically, the crystalline form A exhibits an X-ray powder diffraction spectrum comprising diffraction peaks at 2θangles of 6.68°±0.2°, 9.58°±0.2°, 10.08°±0.2°, 10.41°±0.2°, 11.37°±0.2°, 11.72°±0.2°, 13.30°±0.2°, 13.79°±0.2°, 14.78°±0.2°, 15.71°±0.2°, 15.96°±0.2°, 16.81°±0.2°, 17.89°±0.2°, 19.19°±0.2°, 20.02°±0.2°, 20.71°±0.2°, 21.75°±0.2°, 23.66°±0.2°, 24.61°±0.2°, 25.65°±0.2°, 26.38°±0.2°, 26.59°±0.2° and 28.96°±0.2°, and the crystalline form A exhibits a differential scanning calorimetry curve comprising an endothermic peak at 176.5° C.±3° C.

Figure 2:
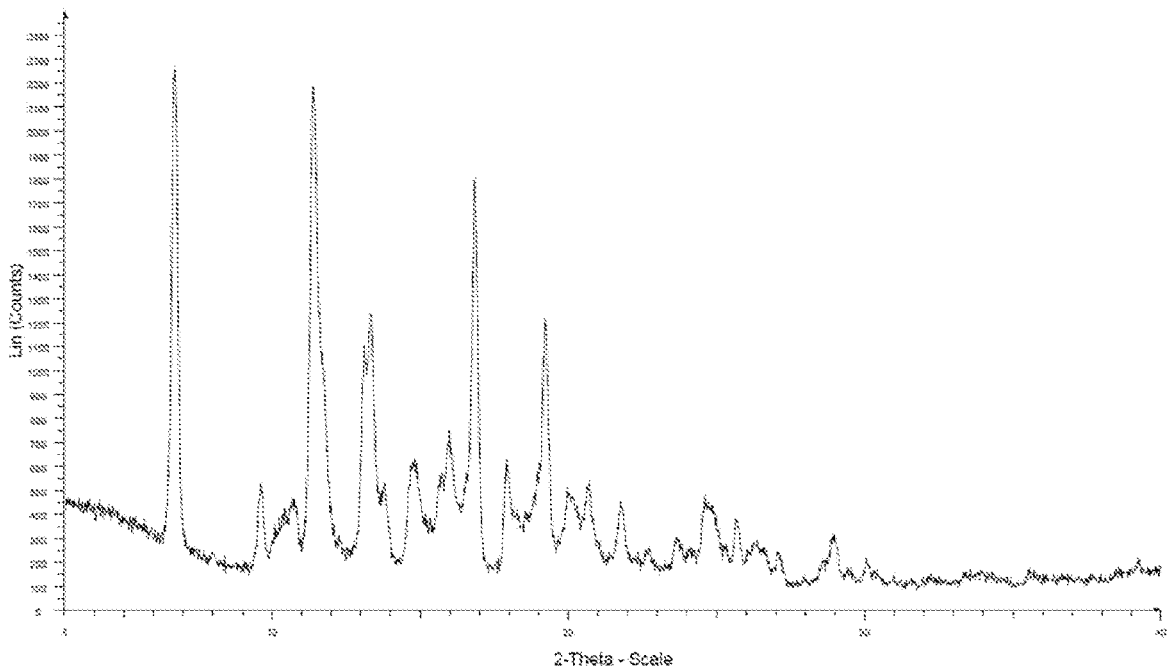
FIG. 2 shows an X-ray powder diffraction (XRPD) spectrum of hydrochloride salt crystalline form A of Compound 1 prepared in Example 3.
Figure 3:
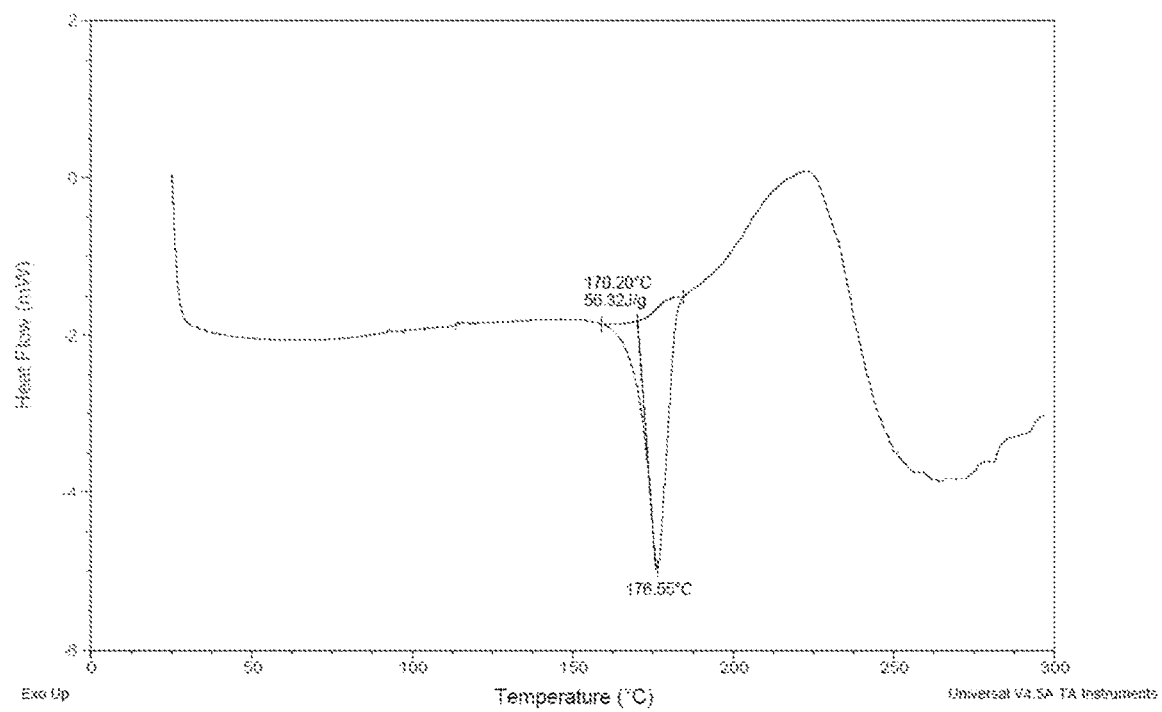
FIG. 3 shows a differential scanning calorimetry (DSC) curve of hydrochloride salt crystalline form A of Compound 1 prepared in Example 3.

More specifically, the crystalline form A is characterized in that (1) its X-ray powder diffraction spectrum is substantially identical to FIG. 2, and/or (2) its differential scanning calorimetry curve is substantially identical to FIG. 3. In the present disclosure, the crystalline form of the salt of the bile acid derivative represented by Formula (S-1) is produced according to the aforementioned method of preparing the salt of the bile acid derivative, wherein the first solvent may be methanol or isopropanol; the second solvent is ethyl acetate or methyl tert-butyl ether; in the reaction, when the first solvent is isopropanol and the second solvent is ethyl acetate, their volume ratio is 1:(1-5) or 1:(2-4); when the first solvent is methanol and the second solvent is methyl tert-butyl ether, their volume ratio of is 1:(1-4) or 1:(2-3).

The present disclosure further provides a crystalline form of a salt of a bile acid derivative represented by Formula (S-9), named as crystalline form B,

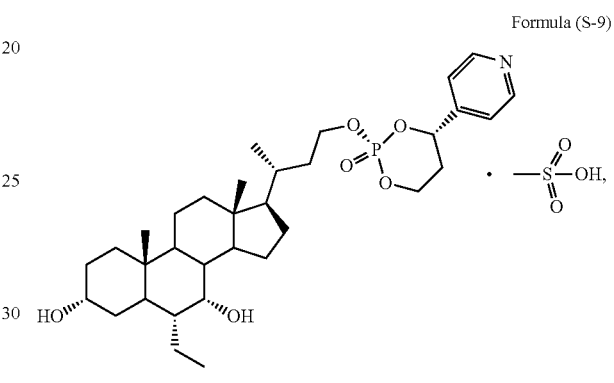

Formula (S-9)

wherein the crystalline form B exhibits an X-ray powder diffraction spectrum comprising diffraction peaks at 2θangles of 4.52°±0.2°, 5.20°±0.2°, 13.34°±0.2°, 13.58°±0.2°, 14.88°±0.2. More specifically, the crystalline form B exhibits an X-ray powder diffraction spectrum comprising diffraction peaks at 2θangles of 4.52° 0.2°, 5.20°±0.2°, 7.12°±0.2°, 9.05°±0.2°, 13.34°±0.2°, 13.58°±0.2°, 14.88°±0.2°, 15.71°±0.2°, 17.48°±0.2° and 18.15°±0.2°. Furthermore specifically, the crystalline form B exhibits an X-ray powder diffraction spectrum comprising diffraction peaks at 2θangles of 4.52° 0.2°, 5.20°±0.2°, 7.12°±0.2°, 9.05°±0.2°, 10.15°±0.2°, 10.72°±0.2°, 13.34°±0.2°, 13.58°±0.2°, 14.26°±0.2°, 14.88°±0.2°, 15.15°±0.2°, 15.71°±0.2°, 17.48°±0.2°, 18.15°±0.2°, 19.72°±0.2°, 20.19°±0.2°, 20.35°±0.2°, 21.22°±0.2°, 22.74°±0.2°, 23.44°±0.2°, 23.99°±0.2° and 32.03°±0.2°.

Figure 5:
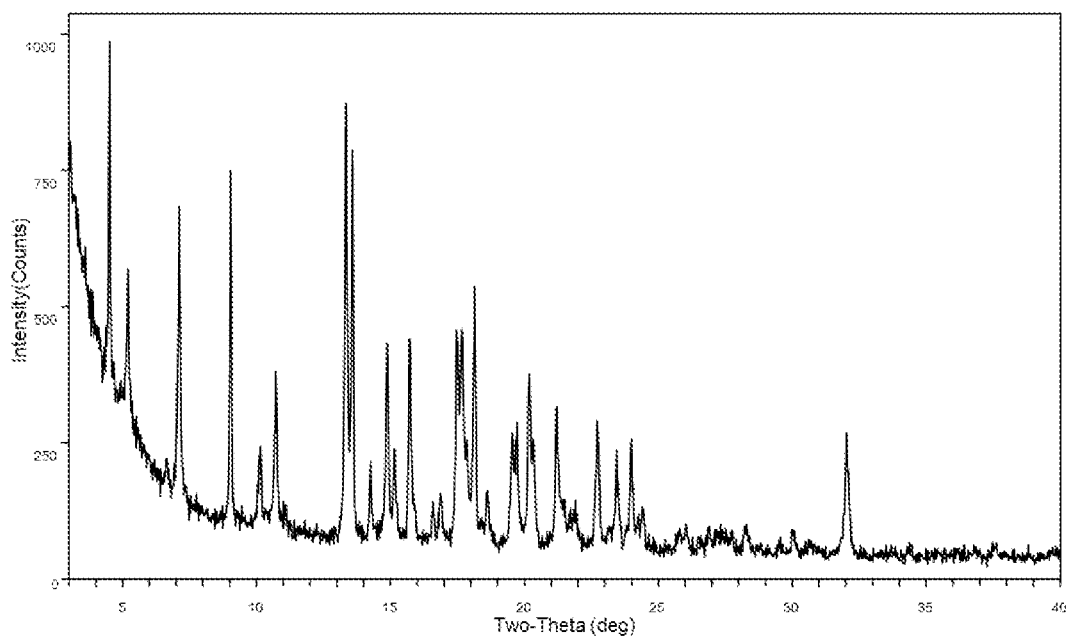
FIG. 5 shows an X-ray powder diffraction (XRPD) spectrum of mesylate salt crystalline form B of Compound 1 prepared in Example 9.
Figure 6:
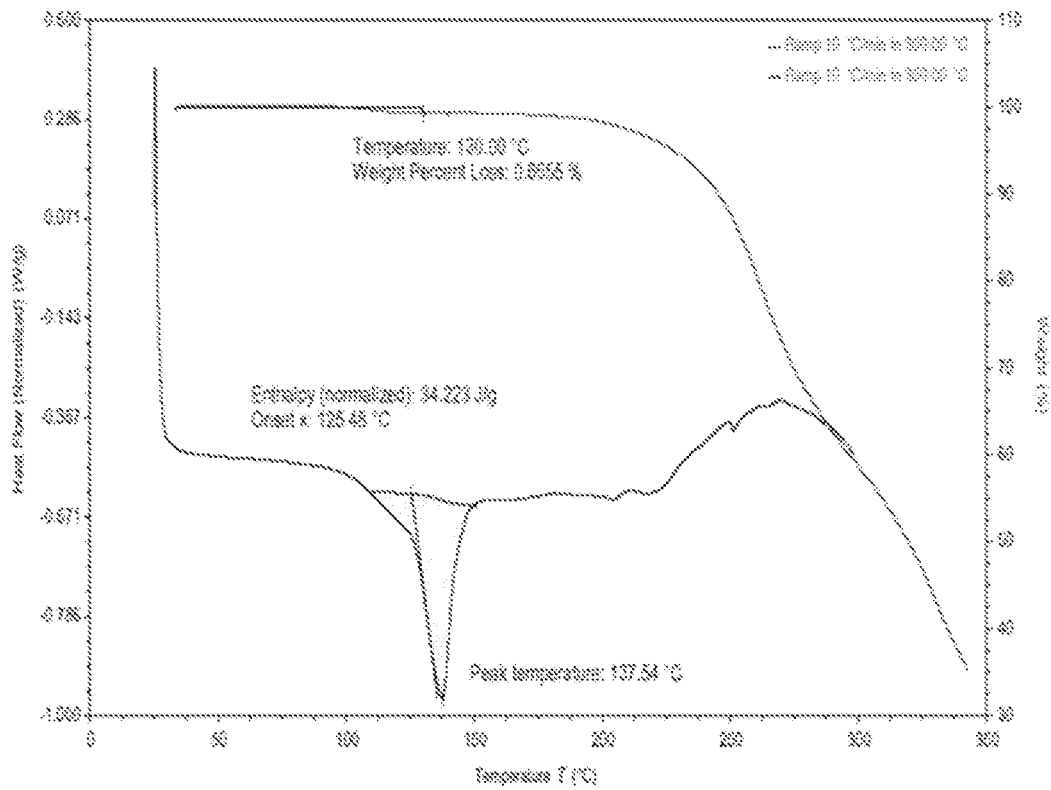
FIG. 6 shows differential scanning calorimetry (DSC) and thermogravimetric analysis (TGA) curves of mesylate salt crystalline form B of Compound 1 prepared in Example 9.

More specifically, the crystalline form B is characterized in that (1) its X-ray powder diffraction spectrum is substantially identical to FIG. 5, and/or (2) its differential scanning calorimetry curve and thermogravimetric analysis curve are substantially identical to FIG. 6.

In the present disclosure, the crystalline form of salt of the bile acid derivative represented by Formula (S-9) is produced according to the aforementioned method of preparing the salt of the bile acid derivative, wherein the first solvent may be isopropanol, and the volume ratio of isopropanol to the second solvent is 1: (6-10) or 1: (7-8). Specifically, when the second solvent is ethyl acetate, the volume ratio of isopropanol to ethyl acetate in the reaction is 1: (6-10) or 1: (7-8).

The present disclosure further provides a crystalline form of a salt of a bile acid derivative represented by Formula (S-9), named as crystalline form C,

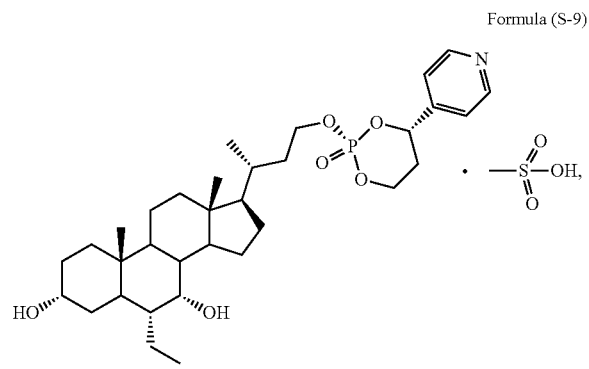

Formula (S-9)

wherein the crystalline form C exhibits an X-ray powder diffraction spectrum comprising diffraction peaks at 2θangles of 6.47°±0.2°, 12.04°±0.2°, 12.53°±0.2°, 13.15°±0.2° and 14.76°±0.2°. More specifically, the crystalline form C exhibits an X-ray powder diffraction spectrum comprising diffraction peaks at 2θangles of 6.47°±0.2°, 9.19°±0.2°, 11.15°±0.2°, 11.39°±0.2°, 12.04°±0.2°, 12.53°±0.2°, 13.15°±0.2°, 14.76°±0.2°, 15.67°±0.2°, 18.48°±0.2°, 18.74°±0.2° and 20.76°±0.2°. More specifically, the crystalline form C exhibits an X-ray powder diffraction spectrum comprising diffraction peaks at 2θ angles of 6.47°±0.2°, 9.19°±0.2°, 10.47°±0.2°, 11.15°±0.2°, 11.39°±0.2°, 12.04°±0.2°, 12.53°±0.2°, 13.15°±0.2°, 14.76°±0.2°, 15.67°±0.2°, 16.06°±0.2°, 17.49°±0.2°, 17.85°±0.2°, 18.13°±0.2°, 18.48°±0.2°, 18.74°±0.2°, 19.19°±0.2°, 19.92°±0.2°, 20.76°±0.2°, 21.02°±0.2°, 21.91°±0.2°, 23.07°±0.2°, 23.90°±0.2° and 24.88°±0.2°.

Figure 7:
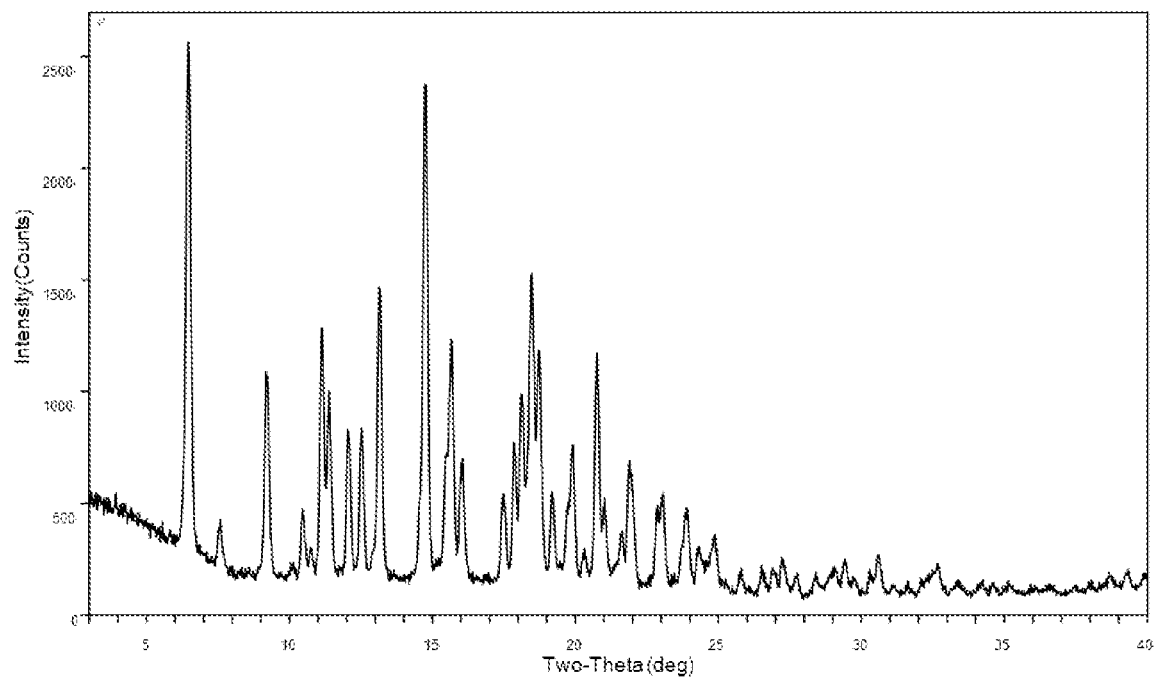
FIG. 7 shows an X-ray powder diffraction (XRPD) spectrum of mesylate salt crystalline form C of Compound 1 prepared in Example 10.
Figure 8:
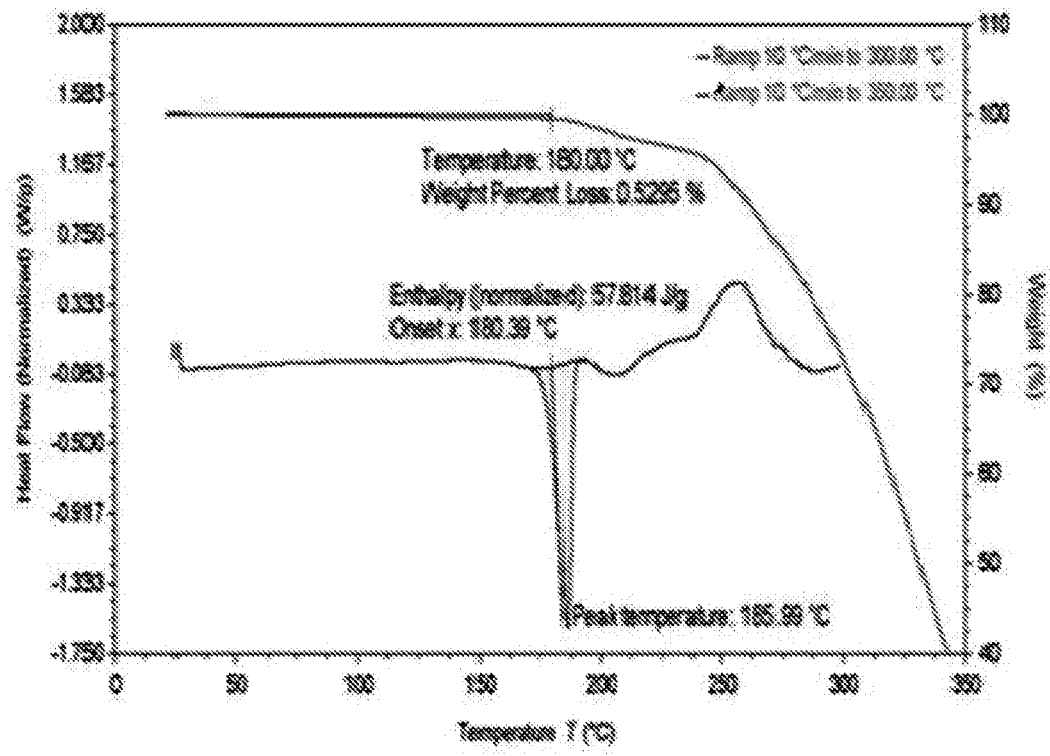
FIG. 8 shows differential scanning calorimetry (DSC) and thermogravimetric analysis (TGA) curves of mesylate salt crystalline form C of Compound 1 prepared in Example 9.

More specifically, the crystalline form C is characterized in that (1) its X-ray powder diffraction spectrum is substantially identical to FIG. 7, and/or (2) its differential scanning calorimetry curve and thermogravimetric analysis curve are substantially identical to FIG. 8.

In the present disclosure, the crystalline form of the salt of the bile acid derivative represented by Formula (S-9) is produced according to the aforementioned method of preparing the salt of the bile acid derivative, wherein the first solvent may be ethanol, and the volume ratio of ethanol to the second solvent is preferably 1: (2-5) or 1: (3-4); and when the second solvent is ethyl acetate, the volume ratio of ethanol to ethyl acetate in the reaction is 1:(2-5) or 1:(3-4).

The present disclosure further provides use of the salt of the bile acid derivative or its solvate or the crystalline form of the salt of the bile acid derivative in manufacture of a medicament for treating or alleviating a FXR-related disease, wherein the FXR-related disease is selected from chronic liver disease, metabolic disease or portal hypertension. The chronic liver disease includes one or more of primary biliary cirrhosis, primary sclerosing cholangitis, liver fibrosis-related disease, drug-induced cholestasis, progressive familial intrahepatic cholestasis, cholestasis of pregnancy, alcoholic liver disease or non-alcoholic fatty liver disease. The portal hypertension is selected from elevated portal pressure caused by liver fibrosis, hepatic sclerosis, splenomegaly or other diseases. The metabolic disease includes hypercholesterolemia, dyslipidemia, cholesterol stone and hypertriglyceridemia.

In the present disclosure, the medicament may contain only the salt of the bile acid derivative as a pharmaceutical active ingredient, and also may contain both the salt of the bile acid derivative and other pharmaceutical compounds, so as to treat or alleviate the above-mentioned chronic liver disease, metabolic disease, portal hypertension or the other diseases. In the use according to the present disclosure, the salt of the bile acid derivative according to the present disclosure may be administered as a single active reagent, or in a combination with other therapeutic agents including the compounds having the same or similar therapeutic activity and being safe and effective for such combination administration. The use for treating, preventing or alleviating diseases or disorders provided by the present disclosure comprises administrating a safe and effective amount of a combination drug containing the salt of the bile acid derivative disclosed in the present disclosure and one or more of therapeutically active agents. In some embodiments, the combination drug contains one or two other therapeutic agents.

In another aspect, the present disclosure provides a method for activating a FXR receptor, comprising administering an effective amount of the salt of the bile acid derivative disclosed in the present disclosure to a subject or sample in need thereof.

In another aspect, the present disclosure provides a method for preventing, treating or alleviating a FXR-related disease, comprising administering to a subject in need thereof a therapeutically effective amount of the salt of the bile acid derivative, the salt of the bile acid derivative in the crystalline form, or the pharmaceutical composition containing the salt of the bile acid derivative disclosed in the present disclosure.

Definitions and General Terms

Unless stated otherwise, the terms used in the description and claims of the present disclosure are defined as following.

Unless stated otherwise, all technical and scientific terms used in the present disclosure have the same meaning as commonly understood by a person skilled in the art. All patents and publications referred to in the present disclosure are incorporated by reference in their entirety. The term "containing" or "comprising" is open-ended, which includes the contents specified in the present disclosure, and does not exclude other contents.

The term "pharmaceutically acceptable" means that a substance or composition must be chemically and/or toxicologically compatible with the other ingredients containing the formulation and/or with the mammal to be treated using it.

The term "equivalent" or its abbreviation "eq." used in the present disclosure is the equivalent amount of other required raw materials based on the basic raw material used in each step (1 equivalent) according to the equivalent relationship of chemical reactions.

In the present disclosure, the crystalline form can be considered as being characterized by the graphical data "depicted" by a graph. These data includes, for example, powder X-ray diffraction spectrums, Raman spectroscopy, Fourier transform-infrared spectroscopy, DSC curves, TGA curves and solid state NMR spectroscopy. The skilled artisan will understand that spectrums of these data may vary slightly (e.g., relative peak intensities and peak positions), resulting from instrument response fluctuations, variations in sample concentration and purity, which is commonly known to the skilled artisan.

Nonetheless, the skilled artisan is able to compare the graphical data in the drawing herein with the graphical data generated from an unknown crystalline form, to determine whether the two set of graphical data characterize the same crystalline form.

Polymorphs can be detected, identified, classified and characterized by well-known techniques such as, but not limited to, differential scanning calorimetry (DSC), thermogravimetric analysis (TGA), X-ray powder diffraction (XRPD), single crystal X-ray diffraction, vibrational spectroscopy, solution calorimetry, solid state nuclear magnetic resonance (SSNMR), Fourier transform infrared spectroscopy (FT-IR spectrum), Raman spectroscopy, hot stage optical microscopy, scanning electron microscopy (SEM), electron crystallography, quantitative analysis, particle size analysis (PSA), surface area analysis, solubility and dissolution rate. Unless stated otherwise, when the text refers to the spectra or data in graphical form (e.g., XRPD, infrared, Raman, and NMR spectra), the term "peak" refers to a peak or other special features identifiable by a person skilled in the art and resulted from non-background noises. The term "effective peak" refers to a peak having at least an intermediate size (e.g., height) of other peaks in the spectrum or data, or at least 1.5, 2, or 2.5 times of an intermediate size of other peaks in the spectrum or data.

As well-known in the field of X-ray powder diffraction (XRPD), for any given crystalline form, all the parameters involved in obtaining an X-ray powder diffraction (XRPD), such as the equipment, humidity, temperature, orientation of powder crystals, may cause some variability in the appearance, intensity and position of peaks in the diffraction spectrum. According to the condition of the instruments employed in the experiments of the present disclose, there is an error tolerance of ±0.2° for the diffraction peaks.

An X-ray powder diffraction spectrum that is "substantially identical" to FIG. 2, FIG. 5 or FIG. 7 provided herein refers to an XRPD spectrum that is considered to be the same with that of the compound shown in the XRPD spectrum of FIG. 2, FIG. 5 or FIG. 7 by a person skilled in the art, more likely they may be slightly different. Such XRPD spectrums may not necessarily show every peak of the diffraction spectrum herein, and/or may show slight changes in the appearance, intensity or shift of the peaks due to differences in the conditions involved in obtaining the data. A skilled person in the art is able to determine whether a crystalline compound sample has the same crystalline form as the crystalline form disclosed herein or not by comparing their XRPD spectrums. Similarly, a skilled person in the art is able to determine whether a given diffraction angle (in 02θ) from an XRPD spectrum is at approximately the same position as the values presented herein. In the context of the present disclosure, the 2θ values in the X-ray powder diffraction spectrum are all in unit of degrees (°).

Similarly, as well-known in the field of differential scanning calorimetry (DSC), in a DSC curve, the melting peak heights depend on many factors related to sample preparation and testing instrument conditions, while the peak positions are relatively unresponsive to experimental details. Accordingly, in some embodiments, the crystalline compounds of the present disclosure are characterized by a DSC curve having characteristic peak positions, having the properties substantially identical to the DSC curve provided in the accompanying drawings of the present disclosure. There is an error tolerance of ±3° C., ±4° C., or ±5° C. for the melting peak, depending on the condition of the instrument used for this test and/or the preparation of the sample. In some specific embodiments, the hydrochloride salt crystalline form A of the present disclosure exhibits an endothermic peak at 176.55° C. with an enthalpy value of 56.32 J/g and an onset temperature of 170.20° C.; the mesylate salt crystalline form B exhibits an endothermic peak at 137.5° C. with an enthalpy value of 34.223 J/g and an onset temperature of 125.5° C.; and the mesylate salt crystalline form C exhibits an endothermic peak at 186° C. with an enthalpy value of 57.814 J/g and an onset temperature of 180.4° C.

As well-known in the field of thermogravimetric analysis (TGA), thermogravimetric analysis (TGA) is a technique for determining the relationship between mass of a substance and temperature at a programmed temperature. The mass change and temperature range shown in the TGA curve depend on factors such as sample preparation and instruments, so the mass change of TGA may vary due to different instruments or samples, and the weight loss rate may have an error tolerance of ±5%, ±4%, ±3% or ±2%. Therefore, the weight loss rate within a certain temperature range measured by TGA should not be considered as an absolute value. In some specific embodiments, the hydrochloride salt crystalline form A of the present disclosure has a weight loss of 2.088% within the temperature range before 170° C.; the mesylate salt crystalline form B has a weight loss of about 0.66% within the temperature range before about 130° C.; and the mesylate salt crystalline form C has a weight loss of about 0.53% within the temperature range before about 180° C.

"Substantially identical" to an X-ray powder diffraction, a DSC curve, a TGA curve, Raman spectroscopy and Fourier transform infrared spectroscopy means that at least 50%, or at least 60%, or at least 70%, or at least 80%, or at least 90%, or at least 95%, or at least 99% of the peaks in the X-ray powder diffraction spectrum, DSC curve, TGA curve, Raman spectroscopy and Fourier transform infrared spectroscopy are shown in the graph.

"Relative intensity" of diffraction peaks in an X-ray powder diffraction spectrum means that when the intensity of the strongest peak among all diffraction peaks in the X-ray powder diffraction spectrum (XRPD) is 100%, the intensity ratio of the other peaks to the strongest peak.

In the present disclosure, the hydrochloride salt crystalline form A of the compound represented by Formula (I) is present in a substantially pure crystalline form.

The term "substantially pure" refers to chemical purity and crystalline form purity, and more specifically, a crystalline form is substantially free of another one or more crystalline forms, that is, the crystalline form has a purity at least 80%, at least 85%, at least 90%, at least 93%, at least 95%, at least 98%, at least 99%, at least 99.5%, at least 99.6%, at least 99.7%, at least 99.8%, or at least 99.9%; or even when the crystalline form contains other crystalline forms, the percentage of the other crystalline forms in the total volume or total weight of the crystalline form is less than 20%, less than 10%, less than 5%, less than 3%, less than 1%, less than 0.5%, less than 0.1%, or less than 0.01%.

In the present disclosure, the purity of the crystals can be determined by using X-ray powder diffraction, thermogravimetric analysis or other methods. The purity of the crystals or mixed crystals of the present disclosure does not need to be 100%, but it may be no less than 80%, preferably no less than 90%, more preferably no less than 95%, and most preferably no less than 98%. Purity within this range is preferred to ensure quality.

The terms "about" and "approximately" as used herein generally means within ±10%, suitably within ±5%, especially within 1% of a given value or range. Alternatively, to a person having ordinary skill in the art, the terms "about" and "approximately" indicates within the acceptable standard error of an average value.

According to the present disclosure, a salt of a bile acid derivative, crystalline form structure thereof, their preparation method and application are provided. The salt of the bile acid derivative is produced by reacting the compound having structure of Formula (I) with the acid. The results show that by reacting the compound having structure of Formula (I) with the specific acid, the produced salt has good solubility and stability, and also has FXR receptor agonistic activity, which can relieve cholestasis, reduce portal pressure and improve liver function. It can be used to manufacture drugs for treating or relieving chronic liver disease, metabolic disease, portal hypertension or related diseases.

Hereinafter the technical solutions in the examples of the present disclosure will be described clearly and completely. Apparently, the described examples below are only a part of the embodiments of the present invention, rather than all of them. Based on these examples in the present disclosure, all the other embodiments obtained by a person having ordinary skill in the art without creative labor should fall within the protection scope of the present disclosure.

The compound structure was determined by nuclear magnetic resonance ($^1$H-NMR). $^1$H-NMR shifts (δ) are given in unit of parts per million (ppm). The instrument used for $^1$H-NMR analysis was a Bruker Advance 400 equipped with a B-ACS 120 autosampler system. The solvent for the tests was common deuterated solvents such as deuterated chloroform ($CDCl_3$), deuterated methanol ($CD_3OD$) or deuterated dimethyl sulfoxide (DMSO-$d_6$). The LC-MS measurement was Agilen-6120Quadrupole LC/MS Mass spectrometer.

The obtained solid form of the salt was analyzed by X-ray powder diffraction (XRPD). The solid samples obtained in the experiments were analyzed by using a D8 advance powder X-ray diffraction analyzer (Bruker) and a D2 phaser powder X-ray diffraction analyzer (Bruker). The instruments are equipped with a LynxEye detector. The D8 advance powder X-ray diffraction analyzer (Bruker) tested the samples using Cu Kα radiation, with 2θ scan angles from 3° to 40° and a scan step of 0.02°. The phototube voltage and phototube current when testing the sample were 40 KV and 40 mA, respectively. The D2 phaser powder X-ray diffraction analyzer (Bruker) tested the samples using Cu Kα radiation, and the phototube voltage and phototube current when testing the sample were 30 KV and 10 mA, respectively.

The obtained solid forms of the compounds or salts were analyzed by polarizing light microscopy (PLM), using an instrument model ECLIPSE LV100POL polarizing microscope (Nikon, Japan).

The obtained solid form of the salt was analyzed by thermogravimetric analysis (TGA), using a thermogravimetric analyzer with a model TGA Q500 or Discovery TGA 55 (TA, United States). The sample was placed at an equilibrated open aluminum sample tray, and weighed automatically inside the TGA heating furnace, and then heated to the final temperature at a rate of 10° C./min.

The obtained solid form of the salt was analyzed by differential scanning calorimetry (DSC), using a differential scanning calorimetry analyzer with a model DSC Q200 or Discovery DSC 250 (TA, United States). The sample was accurately weighed and placed at a DSC puncture sample tray, with its exact mass recorded. The sample was heated to the final temperature at a ramp rate of 10° C./min.

The obtained solid form of the salt was analyzed by dynamic vapor sorption (DVS), using a dynamic vapor sorption analyzer with a model IGA Sorp (Hidentity Isochema). The samples are measured in gradient mode and tested over a humidity range of 0% to 90% with 10% humidity increments for each gradient.

Unless otherwise specified in the examples, the reaction temperature was a room temperature ranging from 20° C. to 30° C.

HPLC represents high performance liquid chromatography. HPLC measurements was performed using an Agilent 1200 high pressure liquid chromatography (Zorbax Eclipse Plus $C^{18}$ 150×4.6 mm column).

The crystalline form can be prepared by many methods including, but being not limited to, crystallization or recrystallization from a suitable solvent mixture, sublimation, solid state transformation from another phase, liquid crystallisation from supercritical fluids and spraying.

The cooled crystallization mixture can be filtered under vacuum and the isolated solid product can be washed with a suitable solvent (e.g., cold recrystallization solvent).

After washing, the product can be dried under a nitrogen purge to obtain the desired crystalline form. The product can be analyzed by suitable spectroscopic or analytical techniques including, but not limited to, for example, X-ray single crystal diffraction analysis, X-ray powder diffraction (XRPD) analysis, differential scanning calorimetry (DSC), thermogravimetric analysis (TGA), Fourier transform-infrared spectroscopy (FT-IR) analysis and Raman spectroscopy (Raman spectroscopy) analysis, to ensure that the crystalline form of the compound has been formed.

The following abbreviations are used throughout the present disclosure:
ACN: acetonitrile;
DCM: dichloromethane;
EtOH: ethanol;
EA, EtOH ethyl acetate;
g: gram;
IPA: isopropanol;
MTBE: methyl tert-butyl ether;
MeOH: methanol;
M, mol/L: mole per liter, that is, amount of substance of the solute contained in 1 L of a solution;
mL, ml: milliliter;
mmol: millimole;
v: volume.

The ratios of solvents in the following examples are volume ratios unless otherwise specified.

EXAMPLES (I) Preparation Examples

Example 1: Synthesis of Compound 1

Compound 1, a white-like solid, was prepared by using the method recited in Example 1 of the patent CN201810930184.X.

The solid was analyzed by polarized light microscopy (PLM) analysis, showing no birefringence. Its DSC-TGA spectrum was shown in FIG. 1. The onset temperatures of the two endothermic peaks of DSC were located at 41.6° C. and 72.6° C., respectively. TGA showed a weight loss of 6.2% before 100° C. DVS showed a hygroscopicity ranging from 1.933%-7.0146% under the condition of a humidity of 10%-90%. Compound 1 exhibited a low melting point and easy hygroscopicity, which was unfavourable for formulation. XRPD showed that this solid was in an amorphous state, and the compound of Example 1 had low melting point, which was unfavourable for formulation.

Example 2 Preparation of the Hydrochloride Salt of Compound 1

At room temperature, the compound of Example 1 (1.0 eq.) was added to 40-60 µL of MeOH and stirred to dissolve it. Then, 1.5 µL of hydrochloric acid (1.0 eq.) was added and stirred, and no solid precipitated. Then, 100 µL ACN was added, and no solid precipitated. After the reaction flask was capped, the resultant was slowly volatilized at room temperature to obtain a solid. The obtained solid sample was tested. XRPD showed that this solid had no significant diffraction peak, indicating that it was in an amorphous state.

UPLC-MS: (m/z): 590.3610 [M+H]+;

$^1$H-NMR (DMSO-$d_6$, 400 MHz, ppm): 8.98 (d, J=6.8 Hz, 2H), 8.03 (d, J=6.8 Hz, 2H), 6.02 (t, J=2.8 Hz, 1H), 4.59 (m, 1H), 4.47 (m, 1H), 4.16 (m, 2H), 3.50 (brs, 1H), 3.14 (m, 1H), 2.42 (m, 1H), 2.16 (m, 1H), 1.91 (m, 1H), 1.81 (m, 2H), 1.77 (m, 1H), 1.76 (m, 1H), 1.72 (m, 1H), 1.70 (m, 1H), 1.53 (m, 1H), 1.50 (m, 1H), 1.47 (m, 1H), 1.45 (m, 1H), 1.42 (m, 2H), 1.39 (m, 1H), 1.32 (m, 1H), 1.30 (m, 1H), 1.27 (m, 1H), 1.19 (m, 1H), 1.18 (m, 1H), 1.17 (m, 1H), 1.16 (m, 1H), 1.14 (m, 1H), 1.10 (m, 1H), 0.99 (m, 1H), 0.94 (d, 3H), 0.89 (m, 1H), 0.82 (m, 6H), 0.60 (s, 3H);

$^{13}$C-NMR (DMSO-$d_6$, 400 MHz, ppm): 157.56, 157.47, 143.20, 123.65, 77.78, 77.73, 71.04, 68.82, 67.50, 67.45, 67.33, 67.26, 56.12, 50.58, 45.78, 42.54, 41.75, 40.41, 39.78, 36.28, 36.22, 35.99, 35.65, 33.99, 33.11, 32.71, 32.26, 32.19, 30.89, 28.40, 23.55, 23.52, 22.63, 20.87, 18.82, 12.18, 12.09;

P-NMR: (DMSO-$d_6$, 162 MHz, ppm): −6.07.

As can be seen from the $^1$H-NMR results, 4 hydrogens on the pyridine ring had significant chemical shifts, suggesting electron transfer in the pyridine and formation of the hydrochloride salt.

DSC analysis showed that the amorphous solid crude product of the hydrochloride salt of Compound 1 prepared by this method had three onset endothermic peaks at about 84.3, 109.0, 132.0° C. Therefore, the salified solid has a greatly improved melting point as compared with Compound 1.

TGA analysis showed that the amorphous solid crude product of the hydrochloride salt of Compound 1 prepared by this method had a weight loss of 2.4% at about 140° C.

Example 3: Preparation of Crystalline Form a of the Hydrochloride Salt of Compound 1

Compound 1 (1.0 g) was added to 2-3 mL of isopropanol, stirred at 40-60° C. to dissolve it completely, and then slowly added with 150 µL of hydrochloric acid (1.05 eq.). 6-10 mL of EtOAc was slowly added. After stirring, a solid precipitated. After stirring for 2-4 hours, the temperature was slowly lowered. After cooling to room temperature, the mixture was continued to be stirred for 1-2 hours and filtered. The obtained solid was dried at 60-70° C. overnight.

(1) The $^1$H-NMR test results were basically consistent with those in Example 2. The 4 hydrogens on the pyridine ring have obvious chemical shifts, demonstrating the formation of the hydrochloride salt. The hydrochloride salt of Compound 1 prepared by above-mentioned method was further tested.

(2) Chloride ion content was measured by using a Shimadzu ion chromatography system, PDM-IC-001. The result showed that the chloride ion content in the sample was 5.6%. Theoretically, the chloride ion content in monohydrochloride salt is 5.8%. Thus, this result indicated that the hydrochloride salt of Compound 1 of Example 2 was prepared by using this method, and the stoichiometry of Compound 1 and the hydrochloric acid was 1:1.

(3) X-ray powder diffraction: The obtained solid was detected by XRPD. The obtained spectrum is shown in FIG. 2. FIG. 2 shows significant diffraction peaks, indicating that this solid was in a crystalline state, and thus this solid was identified as crystalline form A of the hydrochloride salt of Compound 1. Its data results are shown in Table 2. The position of the diffraction peak may have an error tolerance of ±0.2°.

TABLE 2

X-ray powder diffraction analysis results of crystalline form A

| peak position [°2θ] | d-spacing [Å] | peak height | relative peak intensity/I % |
|---|---|---|---|
| 6.683 | 13.2157 | 1996 | 100 |
| 9.579 | 9.2254 | 317 | 15.9 |
| 10.076 | 8.7711 | 125 | 6.3 |
| 10.406 | 8.4938 | 167 | 8.4 |
| 10.739 | 8.2312 | 196 | 9.8 |
| 11.371 | 7.7754 | 1924 | 96.4 |
| 11.723 | 7.5425 | 735 | 36.8 |
| 13.302 | 6.6508 | 1022 | 51.2 |
| 13.791 | 6.4157 | 306 | 15.3 |
| 14.777 | 5.9898 | 348 | 17.4 |
| 15.705 | 5.638 | 194 | 9.7 |
| 15.958 | 5.5491 | 357 | 17.9 |
| 16.808 | 5.2705 | 1621 | 81.2 |
| 17.891 | 4.9539 | 383 | 19.2 |
| 19.191 | 4.6209 | 923 | 46.2 |
| 20.017 | 4.4322 | 221 | 11.1 |
| 20.705 | 4.2864 | 300 | 15 |
| 21.752 | 4.0824 | 249 | 12.5 |
| 22.735 | 3.908 | 75 | 3.8 |
| 23.661 | 3.7572 | 114 | 5.7 |
| 24.608 | 3.6147 | 256 | 12.8 |
| 25.652 | 3.4698 | 166 | 8.3 |
| 26.377 | 3.3761 | 115 | 5.8 |
| 26.593 | 3.3491 | 108 | 5.4 |
| 27.085 | 3.2894 | 93 | 4.7 |
| 28.567 | 3.1221 | 85 | 4.3 |
| 28.958 | 3.0808 | 203 | 10.2 |
| 30.065 | 2.9698 | 95 | 4.8 |
| 33.981 | 2.6361 | 55 | 2.8 |
| 39.241 | 2.294 | 71 | 3.6 |

(4) DSC tested crystalline form A of the hydrochloride salt of Compound 1 prepared in Example 3. The obtained DSC spectrum is shown in FIG. 3.

Crystalline form A exhibited an endothermic peak at about 176.55° C., with an enthalpy of 56.32 J/g and an onset temperature (onset) of 170.20° C. It can be considered that the compound has a melting point of 170° C., which is significantly improved as compared with unsalified Compound 1 and the amorphous hydrochloride salt.

Figure 4:
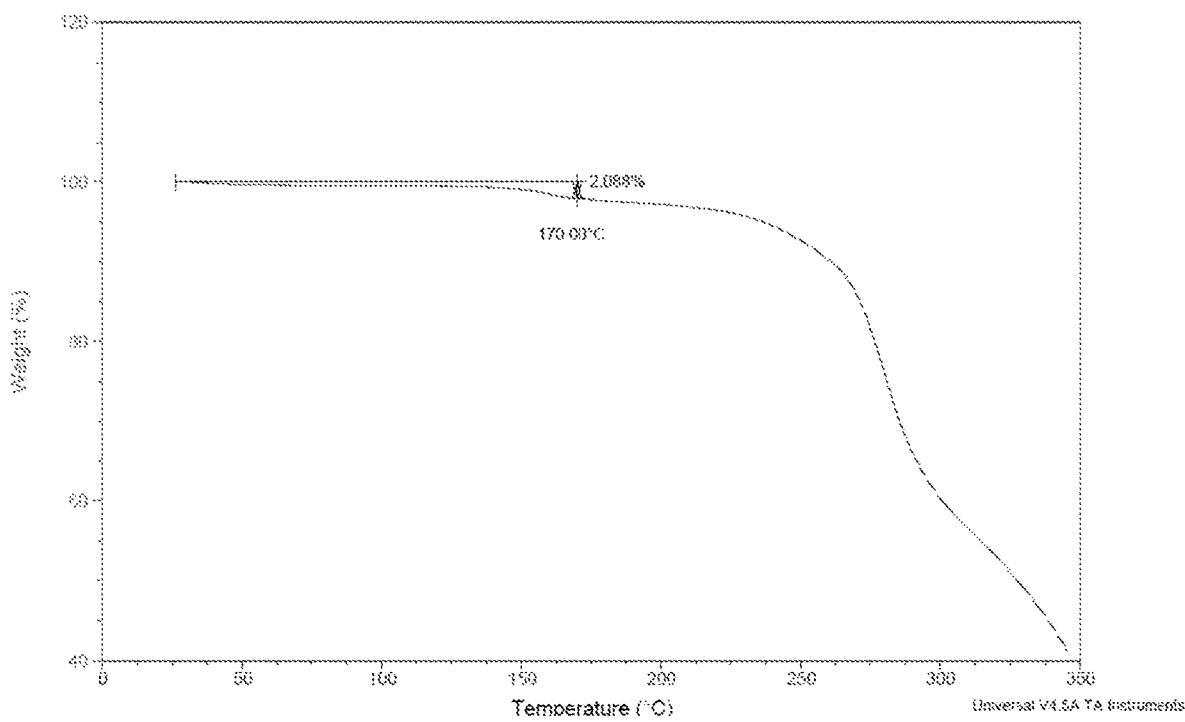
FIG. 4 shows a thermogravimetric analysis (TGA) curve of hydrochloride salt crystalline form A of Compound 1 prepared in Example 3.

(5) TGA tested crystalline form A of the hydrochloride salt of Compound 1 prepared in Example 3. The obtained TGA spectrum is shown in FIG. 4.

The result showed that this sample had a weight loss of 2.088% before about 170° C., indicating that the sample is free of crystal water.

Substitution of some equivalent conditions for the crystallization method may results in a hydrochloride salt solid exhibiting a different XRPD spectrum, sometimes with additional peaks, but exhibiting similar thermal properties on TGA and DSC. These differences in XRPD are resulted from crystallinity, preferred orientation, etc. When the residual content of the crystalline form is different, the obtained hydrochloride salt crystalline form A solid may exhibit different thermal properties on TGA and DSC. As long as it contains the main diffraction peaks in Table 2, at 9.58°±0.2°, 13.79°±0.2°, 16.81°±0.2°, and 19.19°±0.2°, or the main diffraction peaks at 6.68°±0.2°, 9.58°±0.2°, 11.37°±0.2°, 13.30°±0.2°, 13.79°±0.2°, 16.81°±0.2° and 19.19°±0.2°, or the main diffraction peaks at 6.68°±0.2°, 9.58°±0.2°, 11.37°±0.2°, 11.72°±0.2°, 13.30°±0.2°, 13.79°±0.2°, 14.78°±0.2°, 15.96°±0.2°, 16.81°±0.2°, 17.89°±0.2°, 19.19°±0.2°, 20.02°±0.2°, 20.71°±0.2°, 21.75°±0.2°, 24.61°±0.2° and 28.96°±0.2°, the hydrochloride salt crystalline form A is considered to be obtained.

Combining the compound with a suitable acid via ionic or covalent bonds can change the charge distribution in the molecule, adjust the physicochemical properties of the active molecule, and favor for obtaining a variety of solid forms after salt formation. For the hydrochloride salt crystalline form A obtained according to the preparation method of this example, it can be seen from the DSC curves that the crystalline form A has a significantly improved melting point as compared with the amorphous hydrochloride salt prepared in Example 2.

Example 4: Preparation of Oxalate Salt

At room temperature, 10.9 mg of the compound of Example 1 was added in 40-60 µL of MeOH and stirred to dissolve it. Then, 1.665 mg of oxalic acid was added, and no solid precipitated. Then, 120-150 µL of EtOAc was added, and no solid precipitated. The solvent was evaporated to dryness and the resulting solid sample was then characterized. XRPD showed that this solid had only 1 significant diffraction peak, indicating that it was basically in an amorphous state.

Changing to use isopropanol/ethyl acetate (v/v)=1:3, or ethanol/ethyl acetate (v/v)=1:3, no product containing crystalline form was obtained.

Example 5: Preparation of L-Tartrate Salt

At room temperature, 10.9 mg of the compound of Example 1 was added in 120-150 µL of IPA/DCM (v/v=2:1) solution, and stirred with heating at 40-50° C. to dissolve it. Then, L-tartaric acid (2.8 mg, 10 eq.) was added, and no solid precipitated. Then, 300-400 µL EtOAc was added, and no solid precipitated. XRPD showed this solid was in an amorphous state.

Changing to use isopropanol/methyl tert-butyl ether (v/v) =1:3, ethanol/ethyl acetate (v/v)=1:3, or methanol/isopropyl acetate (v/v)=1:4, no product containing crystalline form was obtained.

Example 6: Preparation of p-Toluenesulfonate Salt

At room temperature, 10.4 mg of the compound of Example 1 was added in 50-60 µL of isopropanol, and stirred with heating at 40-50° C. to dissolve it. Then, p-toluenesulfonic acid monohydrate (3.4 mg, 1.0 eq.) was added, and no solid precipitated. Then, 150-200 µL of EtOAc was added, and a viscous sample appeared, but no solids precipitated. The solvent was evaporated to dryness to obtain a solid. $^1$H-NMR (DMSO-$d_6$, 400 MHz) could detect the signal shift of the benzene ring hydrogen of p-toluenesulfonic acid and the pyridine ring hydrogen of Compound 1, indicating the formation of a salt.

Example 7: Preparation of Fumarate Salt

At room temperature, 10.8 mg of the compound of Example 1 was added in 50-60 µL of isopropanol, and stirred with heating at 40-50° C. to dissolve it. Then, p-fumaric acid (2.0 mg, 1.0 eq.) was added, and no solid precipitated. Then, 150-200 µL EtOAc was added, and a viscous sample appeared, but no solid precipitated. XRPD showed this solid was in an amorphous state.

Changing to use isopropanol/dichloromethane (v/v)=1:4, ethanol/acetone (v/v)=1:6, or methanol/isopropyl acetate (v/v)=1:4, no product containing crystalline form was obtained.

Example 8: Preparation of Maleate Salt

At room temperature, 10.2 mg of the compound of Example 1 was added in 50-60 µL of isopropanol, and stirred with heating at 40-50° C. to dissolve it. Then, p-maleic acid (2.0 mg, 1.0 eq.) was added, and no solid precipitated. Then, 120-150 µL of 2-butanone was added, and a viscous sample appeared, but no solid precipitated.

Example 9: Preparation Method 1 of Mesylate Salt

At room temperature, 100.9 mg (0.17 mmol) of the compound of Example 1 was added in 100-120 µL of isopropanol and stirred to dissolve it. Then, 11 µL of methanesulfonic acid (0.17 mmol, 1.0 eq.) was added. 700-800 µL of ethyl acetate was added, and a viscous sample appeared. The mixture was stirred for 2-3 days, to obtain a solid. 100-150 µL of ethanol was added at 40-50° C. to clarify the solution. The mixture was stirred for 2-4 hours to obtain a solid. X-ray single crystal diffraction (XRPD) analysis showed that this solid was in a crystalline form, which was identified as the mesylate salt crystalline form B of Compound 1.

(1)$^1$H-NMR (DMSO-$d_6$, 400 MHz, ppm): 8.89 (d, J=6 Hz, 2H), 7.88 (d, J=6 Hz, 2H), 5.95 (m, 1H), 4.52-4.62 (m, 1H), 4.42-4.50 (m, 1H), 4.13-4.18 (m, 2H), 3.50 (brs, 1H), 3.14 (m, 1H), 2.38 (m, 1H), 2.34 (s, 3H), 2.16 (m, 1H), 1.92 (m, 1H), 1.81 (m, 2H), 1.77 (m, 1H), 1.76 (m, 1H), 1.72 (m, 1H), 1.71 (m, 1H), 1.51 (m, 1H), 1.50 (m, 1H), 1.47 (m, 1H), 1.45 (m, 1H), 1.42 (m, 2H), 1.39 (m, 1H), 1.32 (m, 1H), 1.30 (m, 1H), 1.27 (m, 1H), 1.19 (m, 1H), 1.18 (m, 1H), 1.17 (m, 1H), 1.16 (m, 1H), 1.14 (m, 1H), 1.10 (m, 1H), 0.99 (m, 1H), 0.94 (d, 3H), 0.90 (m, 1H), 0.84 (m, 6H), 0.61 (s, 3H).

The methyl signal of methanesulfonic acid was included in the hydrogen spectrum and a significant chemical shift of the 4 hydrogens of the pyridine ring was observed, indicating the formation of the mesylate salt.

(2) The XRPD spectrum of the mesylate salt crystalline form B of the Compound 1 is shown in FIG. 5. The XRPD spectrum includes significant diffraction peaks, indicating that this solid was in a crystalline state. The data results of the mesylate salt crystalline form B prepared in this example are shown in Table 3. The peak positions may have an error tolerance of ±0.2°

TABLE 3

X-ray powder diffraction analysis results of crystalline form B

| peak position [°2θ] | d-spacing [Å] | peak height | relative peak intensity/I % |
|---|---|---|---|
| 4.517 | 19.5474 | 619 | 77.7 |
| 5.204 | 16.9665 | 267 | 33.5 |

TABLE 3-continued

X-ray powder diffraction analysis results of crystalline form B

| peak position [°2θ] | d-spacing [Å] | peak height | relative peak intensity/I % |
|---|---|---|---|
| 7.116 | 12.4123 | 530 | 66.5 |
| 9.045 | 9.7689 | 645 | 80.9 |
| 10.145 | 8.7116 | 135 | 16.9 |
| 10.724 | 8.243 | 284 | 35.6 |
| 13.342 | 6.6308 | 797 | 100 |
| 13.58 | 6.5152 | 710 | 89.1 |
| 14.263 | 6.2046 | 128 | 16.1 |
| 14.877 | 5.9499 | 350 | 43.9 |
| 15.153 | 5.8421 | 157 | 19.7 |
| 15.711 | 5.636 | 364 | 45.7 |
| 16.589 | 5.3396 | 64 | 8 |
| 16.869 | 5.2516 | 77 | 9.7 |
| 17.482 | 5.0687 | 374 | 46.9 |
| 18.146 | 4.8848 | 469 | 58.8 |
| 18.621 | 4.7611 | 69 | 8.7 |
| 19.719 | 4.4985 | 228 | 28.6 |
| 20.193 | 4.394 | 311 | 39 |
| 20.348 | 4.3608 | 187 | 23.5 |
| 21.215 | 4.1845 | 252 | 31.6 |
| 21.905 | 4.0542 | 76 | 9.5 |
| 22.736 | 3.9078 | 220 | 27.6 |
| 23.444 | 3.7914 | 166 | 20.8 |
| 23.992 | 3.706 | 190 | 23.8 |
| 24.413 | 3.6432 | 70 | 8.8 |
| 26.027 | 3.4207 | 46 | 5.8 |
| 28.287 | 3.1523 | 48 | 6 |
| 30.059 | 2.9704 | 40 | 5 |
| 32.031 | 2.7919 | 227 | 28.5 |

(3) The TGA tested the mesylate salt crystalline form B prepared in Example 9, showing a weight loss of about 0.66% before about 130° C., indicating that the sample was free of crystalline water.

(4) The DSC tested the mesylate salt crystalline form B prepared in Example 9, showing an endothermic peak at 137.5° C., with an enthalpy of 34.223 J/g and an onset temperature of 125.5° C. It can be considered that the melting point of the crystalline form is about 125.5° C. The composite spectrum of TGA and DSC is shown in FIG. 6.

When the residual content of the crystalline form is different, the obtained mesylate salt solid may exhibit different thermal properties on TGA and DSC, or exhibit different XRPD spectrums, sometimes show additional peaks. As long as it contains the main diffraction peaks in Table 3 at 2θangles of 4.52°±0.2°, 5.20°±0.2°, 13.34°±0.2°, 13.58°±0.2°, and 14.88°±0.2, or the main diffraction peaks at 2θangles of 4.52° 0.2°, 5.20°±0.2°, 7.12°±0.2°, 9.05°±0.2°, 13.34°±0.2°, 13.58°±0.2°, 14.88°±0.2°, 15.71°±0.2°, 17.48°±0.2° and 18.15°±0.2°, or the main diffraction peaks at 2θangles of 4.52° 0.2°, 5.20°±0.2°, 7.12°±0.2°, 9.05°±0.2°, 10.15°±0.2°, 10.72°±0.2°, 13.34°±0.2°, 13.58°±0.2°, 14.26°±0.2°, 14.88°±0.2°, 15.15°±0.2°, 15.71°±0.2°, 17.48°±0.2°, 18.15°±0.2°, 19.72°±0.2°, 20.19°±0.2°, 20.35°±0.2°, 21.22°±0.2°, 22.74°±0.2°, 23.44°±0.2°, 23.99°±0.2° and 32.03°±0.2°, the mesylate salt crystalline form B is considered to be obtained.

Example 10: Preparation Method 2 of Mesylate Salt

At room temperature, 30.5 mg (0.0517 mmol) of the compound of Example 1 was added in 100-120 μL of ethanol, and stirred to dissolve it. Then, 3.35 μL of methanesulfonic acid (0.0517 mmol, 1.0 eq.) was added. 300-400 μL of ethyl acetate at 40-50° C. was added, and a viscous sample appeared. The mixture was stirred for 30-60 min, to obtain a solid. The X-ray single crystal diffraction (XRPD) analysis showed that this solid was in a crystalline form. The crystalline form prepared in this example was the mesylate salt crystalline form C.

(1) $^1$H-NMR (DMSO-$d_6$, 400 MHz, ppm) was consistent with that in Example 9.

(2) The XRPD spectrum of the mesylate salt crystalline form C prepared in Preparation Example 10 is shown in FIG. 7.

The XRPD spectrum includes significant diffraction peaks, indicating that this solid was in a crystalline state. This solid is identified as the mesylate salt crystalline form C of Compound 1. Its data results are shown in Table 4. The peak positions have an error tolerance of ±0.2°.

TABLE 4

X-ray powder diffraction analysis results of the crystalline form C

| peak position [°2θ] | d-spacing [Å] | peak height | relative peak intensity/I % |
|---|---|---|---|
| 6.467 | 13.6565 | 2269 | 100 |
| 7.588 | 11.6407 | 200 | 8.8 |
| 9.188 | 9.6171 | 918 | 40.5 |
| 10.465 | 8.4462 | 273 | 12 |
| 11.152 | 7.9276 | 1097 | 48.3 |
| 11.389 | 7.763 | 797 | 35.1 |
| 12.043 | 7.3427 | 608 | 26.8 |
| 12.532 | 7.0577 | 648 | 28.6 |
| 13.145 | 6.7299 | 1271 | 56 |
| 14.759 | 5.9973 | 2168 | 95.5 |
| 15.665 | 5.6524 | 1032 | 45.5 |
| 16.055 | 5.5159 | 516 | 22.7 |
| 17.494 | 5.0651 | 327 | 14.4 |
| 17.853 | 4.9642 | 618 | 27.2 |
| 18.126 | 4.89 | 806 | 35.5 |
| 18.48 | 4.7971 | 1310 | 57.7 |
| 18.735 | 4.7323 | 962 | 42.4 |
| 19.19 | 4.6213 | 334 | 14.7 |
| 19.915 | 4.4545 | 562 | 24.8 |
| 20.33 | 4.3646 | 103 | 4.5 |
| 20.764 | 4.2743 | 979 | 43.1 |
| 21.02 | 4.2229 | 325 | 14.3 |
| 21.597 | 4.1113 | 184 | 8.1 |
| 21.907 | 4.0538 | 531 | 23.4 |
| 23.068 | 3.8524 | 404 | 17.8 |
| 23.897 | 3.7205 | 320 | 14.1 |
| 24.329 | 3.6555 | 168 | 7.4 |
| 24.879 | 3.5758 | 227 | 10 |
| 25.803 | 3.45 | 102 | 4.5 |
| 26.52 | 3.3583 | 108 | 4.8 |
| 26.909 | 3.3106 | 112 | 4.9 |
| 27.225 | 3.2728 | 161 | 7.1 |
| 27.755 | 3.2115 | 95 | 4.2 |
| 28.406 | 3.1394 | 79 | 3.5 |
| 29.06 | 3.0702 | 122 | 5.4 |
| 29.413 | 3.0342 | 137 | 6 |
| 30.287 | 2.9486 | 103 | 4.5 |
| 30.595 | 2.9196 | 170 | 7.5 |
| 31.639 | 2.8256 | 54 | 2.4 |
| 32.68 | 2.7379 | 136 | 6 |
| 33.39 | 2.6813 | 61 | 2.7 |
| 34.249 | 2.616 | 58 | 2.6 |
| 35.15 | 2.551 | 53 | 2.3 |
| 38.783 | 2.32 | 57 | 2.5 |
| 39.337 | 2.2886 | 83 | 3.7 |

(3) The TGA tested the mesylate salt crystalline form C prepared in Example 10, showing a weight loss of about 0.53% before about 180° C., indicating that the sample was free of crystalline water.

(4) The DSC tested the mesylate salt crystalline form C prepared in Example 10, showing an endothermic peak at 186° C. with an enthalpy of 57.814 J/g and an onset temperature of 180.4° C. It can be considered that the melting point of the crystalline form is about 180° C. The composite spectrum TGA and DSC is shown in FIG. 8. The TGA and DSC data of the mesylate salt crystalline form B and crystalline form C indicate that crystalline form C has a higher thermal stability as compared to crystalline form B.

When the residual content of the crystalline form is different, the obtained mesylate salt solid may exhibit different thermal properties on TGA and DSC, or exhibit different XRPD spectrums, sometimes show additional peaks. As long as it contains the main diffraction peaks in Table 4 at 2θangles of 6.47°±0.2°, 12.04°±0.2°, 12.53°±0.2°, 13.15°±0.2°, and 14.76°±0.2°; or the main diffraction peaks at 2θangles of 6.47°±0.2°, 9.19°±0.2°, 11.15°±0.2°, 11.39°±0.2°, 12.04°±0.2°, 12.53°±0.2°, 13.15°±0.2°, 14.76°±0.2°, 15.67°±0.2°, 18.48°±0.2°, 18.74°±0.2° and 20.76°±0.2°, or the main diffraction peaks at 6.47°±0.2°, 9.19°±0.2°, 10.47°±0.2°, 11.15°±0.2°, 11.39°±0.2°, 12.04°±0.2°, 12.53°±0.2°, 13.15°±0.2°, 14.76°±0.2°, 15.67°±0.2°, 16.06°±0.2°, 17.49°±0.2°, 17.85°±0.2°, 18.13°±0.2°, 18.48°±0.2°, 18.74°±0.2°, 19.19°±0.2°, 19.92°±0.2°, 20.76°±0.2°, 21.02°±0.2°, 21.91°±0.2°, 23.07°±0.2°, 23.90°±0.2° and 24.88°±0.2°. The mesylate salt crystalline form C may be considered to be obtained.

Example 11: Stability Comparison Between the Hydrochloride Salt Crystalline Form A and the Mesylate Salt Crystalline Form of the Compound 1

The DVS of Compound 1 shows that the hygroscopicity was 1.933%-7.0146% at a humidity of 10-90%. The compound has strong hygroscopicity and is not conducive to preservation. The obtained salt solid form was analyzed by using dynamic vapor sorption (DVS). The hygroscopicity comparison between the hydrochloride salt crystalline form A and the mesylate salt crystalline form C is compared. The results are shown in Table 5.

TABLE 5

DVS analysis results of the hydrochloride salt crystalline form A and the mesylate salt crystalline form C of Compound 1

| test samples | DVS results | solid state (XRPD) after DVS |
|---|---|---|
| Compound 1 | Hygroscopicity was 1.933%-7.0146% at a relative humidity of 10-90% | amorphous powder |
| hydrochloride salt crystalline form A | Hygroscopicity was 0.326-8.03% at a relative humidity of 10%-90%; and hygroscopicity was 3.569% at a relative humidity of 80% | no change in crystalline form after moisture absorption |
| mesylate salt crystalline form C | Hygroscopicity was 0.17-15.03% at a relative humidity of 10%-90%; and hygroscopicity was 6.38% at a relative humidity of 80%. | change to amorphous after moisture absorption |

As can be known from the above table: (1) the overall hygroscopicity of the hydrochloride salt crystalline form A is lower than that of mesylate salt crystalline form C; (2) The hygroscopicity of the hydrochloride salt crystalline form A is small when the relative humidity is lower than 75%; (3) The hydrochloride salt crystalline form A after moisture absorption can still maintain in the crystalline state; the hygroscopicity of the hydrochloride salt crystalline form A is weaker than that of mesylate salt crystalline form C; the hydrochloride salt crystalline form A after moisture absorption has a higher stability that the mesylate salt crystalline form C.

Figure 9:
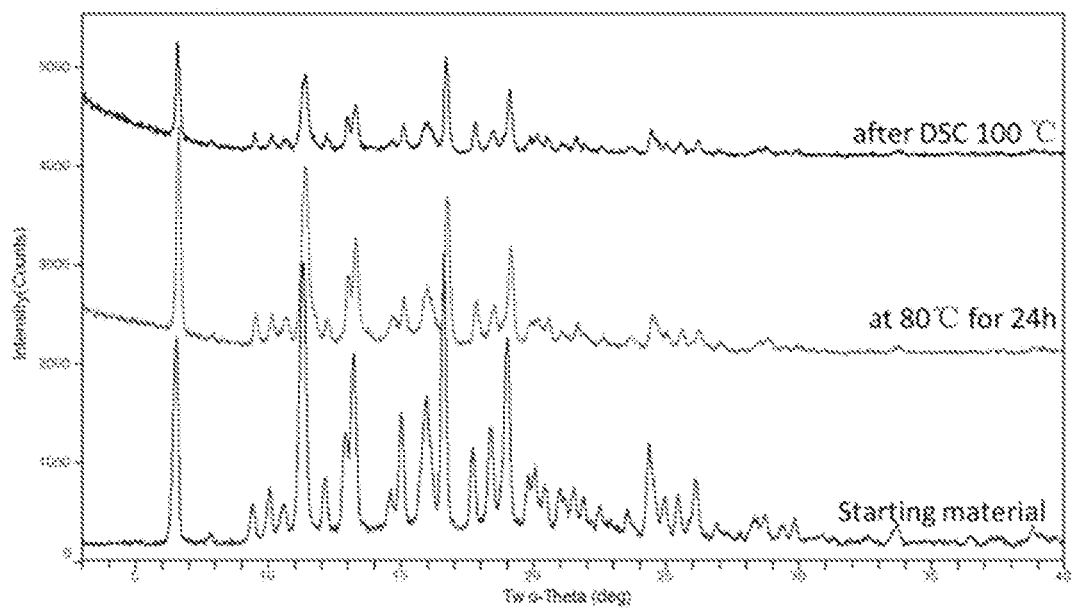
FIG. 9 shows an XRPD spectrum comparison between hydrochloride salt crystalline form A and the hydrochloride salt crystalline form A after being thermally treated.

Example 12: Stability of the Hydrochloride Salt Crystalline Form A of the Compound During Thermal Treatment and Grinding The crystalline form A was heated to 100° C. through programmed temperature or kept at 80° C. for 24 h in DSC. The XRPD detection results of the obtained samples are shown in FIG. 9. The XRPD spectrum shows that the main diffraction peaks of the obtained samples have not change.

Figure 10:
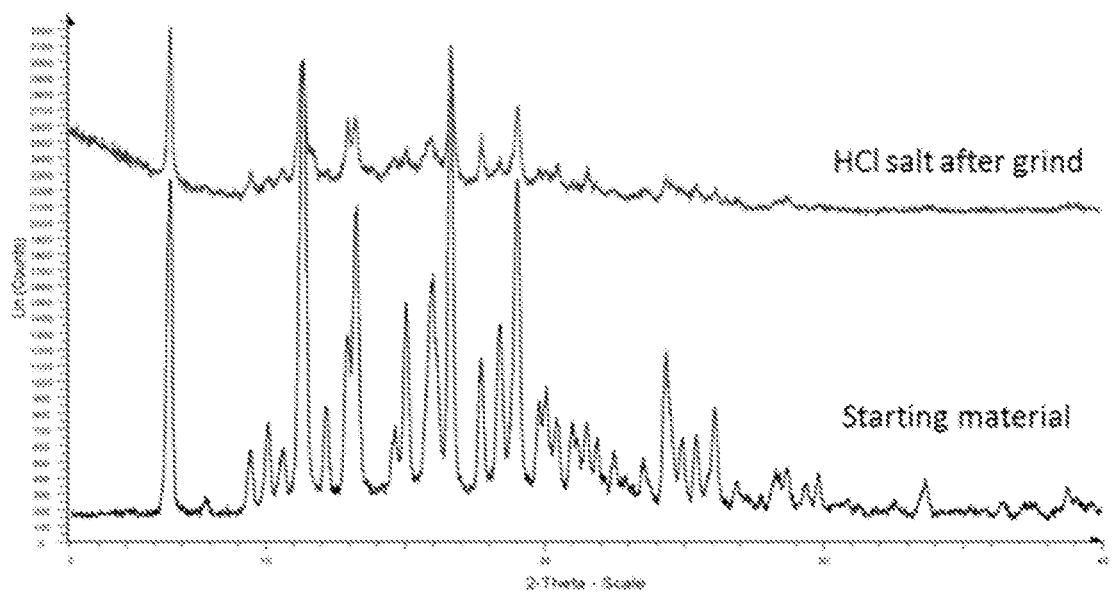
FIG. 10 shows an XRPD spectrum comparison between hydrochloride salt crystalline form A and the hydrochloride salt crystalline form A after being ground.

A certain amount of hydrochloride salt crystalline form A was added to a mortar and ground at room temperature for 5 minutes. The XRPD detection results of the obtained samples are shown in FIG. 10. The XRPD spectrum shows that the main diffraction peaks of the obtained samples have not changed.

To sum up the research results of Example 12 and 13, the hydrochloride salt crystalline form A has a significantly higher melting point than Compound 1, and can maintain in a stable crystalline form during heating and grinding. The hydrochloride salt crystalline form A has a weaker hygroscopicity than the mesylate salt crystalline form C, and the mesylate salt crystalline form C after moisture absorption changes to an amorphous form, whereas the hydrochloride salt crystalline form A still can maintain in the crystalline state. Considering from storage and processing, the solid form of the hydrochloride salt crystalline form A is more suitable for further development.

(II) Effect Example

Effect Example 1: Effects of Compound 1 and the Hydrochloride Salt Prepared in Example 3 on 17α-Ethinylestradiol (E2-17a) Induced Cholestasis in Rats Experimental method: E2-17α was administered by subcutaneous injection in the neck. The test compounds were administered by gavage for 7 days after modeling. After the last day of administration, the rats were fasted but had access to water. The experiment was performed on the next day, and treatment was performed after 24 h. The rats were anesthetized by intraperitoneal injection of 20% urethane (7 ml/kg). After anesthesia, the rats were fixed on a rat board to make a median abdominal incision from the xiphoid process of the upper abdomen downward, with a 3-4 cm incision. The common bile duct was isolated. A PE-10 polyethylene catheter (inner diameter: 0.28 mm, outer diameter: 0.61 mm) was used for intubation operation of the bile ducts. During the operation, the body weight was maintained between 37° C. and 38° C. with warm lamps and air conditioners to prevent changes in bile flow rate at low temperature. After the intubation was completed, the skin was sutured to prevent the water evaporation from the abdominal cavity. The other end of the bile duct cannula was drawn out and flowed into a fixed 0.2 mL collection tube, to consecutively perform collection every 15 min for 8 times.

Before the experiment, the weight of the bile collection tube was accurately weighed and recorded as $B_1$. After the bile collection was completed in the experiment, the total weight of the bile and the collection tube was weighed and recorded as $A_2$. The weight of bile in the tube was calculated by subtracting $B_1$ from $A_2$, and converted into volume according to 1 g/mL. The amount of bile secretion of rats in each group was expressed as mean±standard deviation (Mean±S.D).

Bile Flow Rate (μL/Kg/Min)=($A_2$-$B_1$)×1000000/ Body Weight

After the bile collection, blood was collected from the inferior vena cava of rats. The blood samples were allowed to stand for 2 h at room temperature, and centrifuged at 4000 rpm for 15 min. The serum was routinely separated to detect ALT, AST, and ALP. The left serum was aliquoted and frozen at −20° C. for subsequent detection.

The experimental results indicate that the hydrochloride salt of Compound 1 has a superior effect of promoting bile excretion over Compound 1. Compared with the E2-17α group, Compound 1 and the hydrochloride salt of Compound 1 have significantly increased strength for promoting bile excretion. The biliary excretion amount after 120 minutes of the administration of Compound 1 and the hydrochloride salt is still higher than that in the model group (E2-17α group). This demonstrates that Compound 1 and its hydrochloride salt have therapeutic effects on the diseases related to bile excretion disorders.

Effect Example 2: Efficacy of the Hydrochloride Salt of Compound 1 Against AMLN Diet-Induced NASH in Ob/Ob Mice Test method: (1) $C_{57}$ mice and ob/ob mice were adaptively reared for 1 week. ① The C57 mice were given LFD diet (normal mouse group), and the ob/ob mice were divided into two groups: ② 15 mice were given LFD diet (blank control group), and the rest were given AMLN diet (containing 40 kcal % fat, 20 kcal % fructose and 2% cholesterol) for 14 weeks. (2) Sampling for pathology detection: C57+ LFD diet group (n=3), ob/ob+ AMLN diet group (n=3), liver lesions were evaluated according to NAFLD activity score to estimate the degree of model construction; the mice in the ob/ob+ AMLN diet group were tested for fasting blood glucose (FBG); and blood was collected from the eye socket. The serum was separated, and ALT and insulin (INS) in the serum were detected. (3) Insulin resistance (HOMA-IR) was calculated according to HOMA-IR=INS(μ/mL)×FBG (mM)/22.5.

The experimental results show that the hydrochloride salt of Compound 1 can significantly reduce the total score of the AMLN diet-induced $Lep^{ob}/Lep^{ob}$ mouse NASH model, reduce intralobular inflammation and hepatocyte ballooning in AMLN diet-induced $Lep^{ob}/Lep^{ob}$ mice NASH model, inhibit the further development of NASH disease process, and also can significantly reduce liver fibrosis in NASH mice. Moreover, the hydrochloride salt of Compound 1 can significantly reduce the levels of ALT and AST in the serum of mice, exhibiting repairing and protective effects on liver injury in NASH mice.

The description of the examples above is just used to facilitate understanding of the method and core concept of the present disclosure. It should be noted that for those skilled in the art, without departing from the principle and scope of the present invention, various improvements and modifications can also be made to the present invention, and these improvements and modifications should also fall within the scope of protection of the present invention.

The invention claimed is:

1. A salt of a bile acid derivative, produced by reacting a compound having structure of Formula (I) with an acid; or a solvate of the salt of the bile acid derivative;

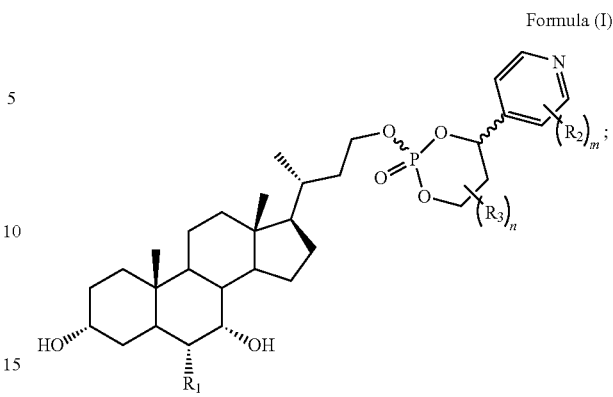

Formula (I)

wherein $R_1$ is hydrogen, substituted or unsubstituted C1-C12 alkyl or halogen;
each $R_2$ is independently any one or more selected from substituted or unsubstituted C1-C12 alkyl, halogen, cyano, hydroxyl, nitro, a sulfo group and carboxyl;
m is 0, 1, 2, 3 or 4;
each $R_3$ is independently one or more selected from substituted or unsubstituted C1-C12 alkyl, halogen, hydroxyl, C6-C30 aryl;
n is 0, 1, 2, 3, 4 or 5;
the acid is an inorganic acid or an organic acid;
the inorganic acid is selected from hydrochloric acid;
the organic acid is selected from methanesulfonic acid, oxalic acid, p-toluenesulfonic acid, L-tartaric acid, fumaric acid or maleate.

2. The salt of the bile acid derivative according to claim 1, wherein the $R_1$ is hydrogen, substituted or unsubstituted C2-C6 alkyl or halogen; or
$R_1$ is hydrogen, fluorine, chlorine, bromine, methyl, ethyl, n-propyl, isopropyl, n-butyl, isobutyl, tert-butyl, n-pentyl, isoamyl or n-hexyl.

3. The salt of the bile acid derivative according to claim 1, wherein each $R_2$ is independently any one or more selected from substituted or unsubstituted C2-C6 alkyl, halogen, cyano, hydroxyl, nitro, a sulfo group, and carboxyl; or
each $R_2$ is independently fluorine, chlorine, bromine, methyl, ethyl, n-propyl, isopropyl, n-butyl, isobutyl, tert-butyl, n-pentyl, isoamyl, n-hexyl, hydroxyl, nitro, a sulfo group and carboxyl.

4. The salt of the bile acid derivative according to claim 1, wherein each $R_3$ is independently one or more selected from substituted or unsubstituted C2-C6 alkyl, halogen, hydroxyl, C6-C18 aryl; or
each $R_3$ is independently fluorine, chlorine, bromine, methyl, ethyl, n-propyl, isopropyl, n-butyl, isobutyl, tert-butyl, n-pentyl, isoamyl, n-hexyl, hydroxyl, phenyl, naphthyl, anthracenyl or phenanthryl.

5. The salt of the bile acid derivative according to claim 1, wherein the compound represented by Formula (I) is Formula (F-1), Formula (F-2), Formula (F-3), Formula (F-4), Formula (F-5), Formula (F-6), Formula (F-7), Formula (F-8), (F-9), Formula (F-10), Formula (F-11), Formula (F-12), (F-13), Formula (F-14), Formula (F-15), Formula (F-16), (F-17), Formula (F-18), Formula (F-19), Formula (F-20), (F-21), Formula (F-22), Formula (F-23), Formula (F-24), (F-25), Formula (F-26), Formula (F-27), Formula (F-28), (F-29), Formula (F-30), Formula (F-31) or Formula (F-32), Formula (F-1)
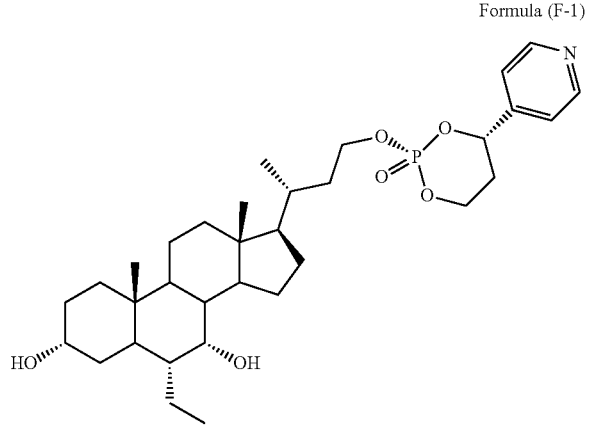
Formula (F-5)
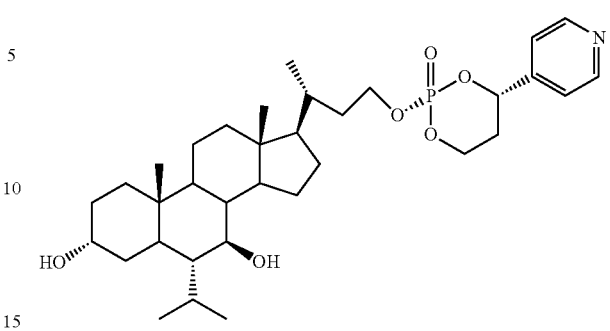
Formula (F-2)
Formula (F-6)
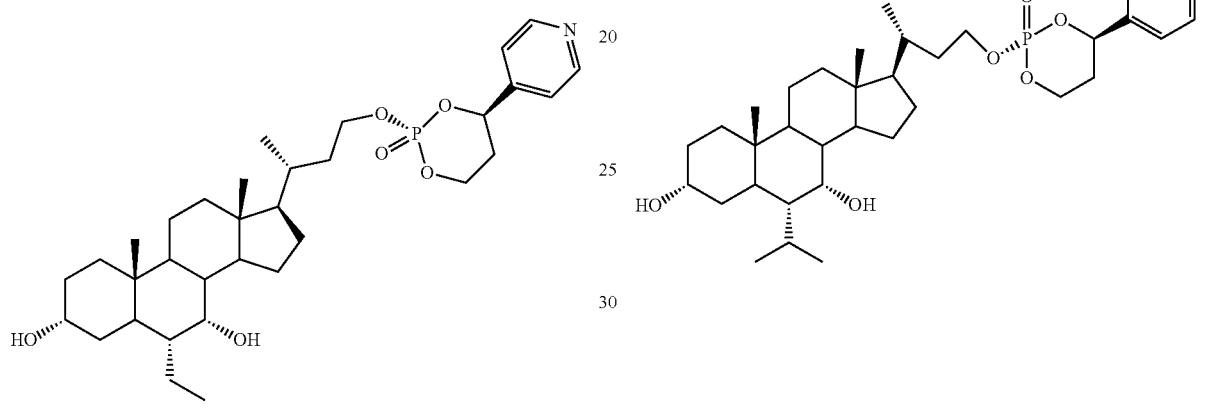
Formula (F-3)
Formula (F-7)
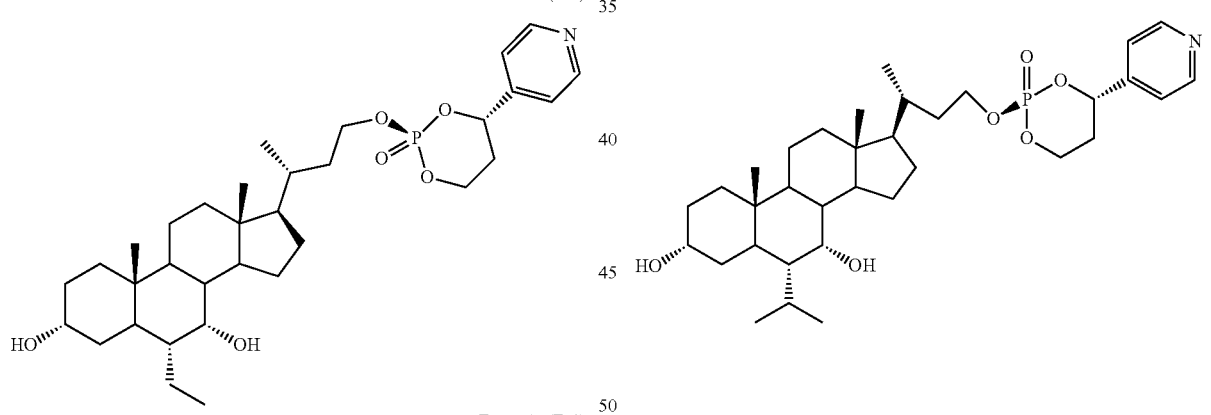
Formula (F-4)
Formula (F-8)
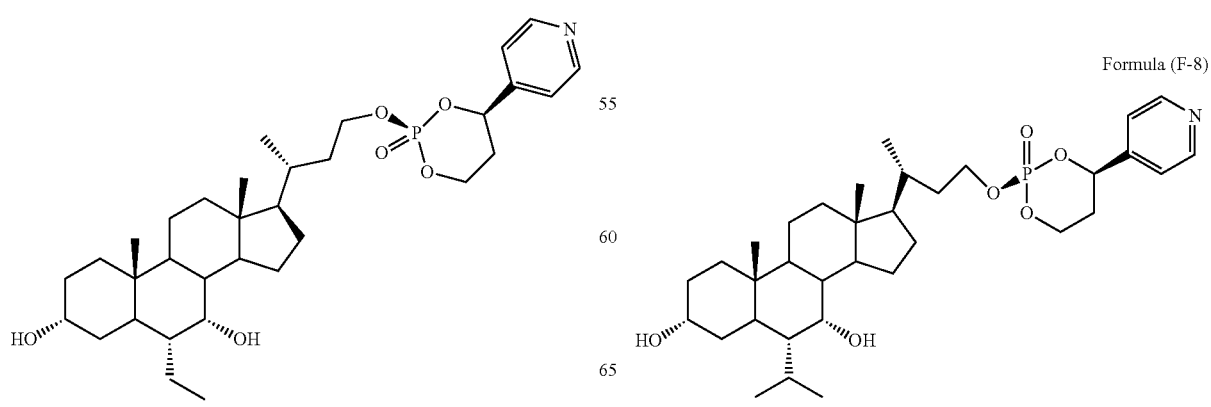

Formula (F-9)
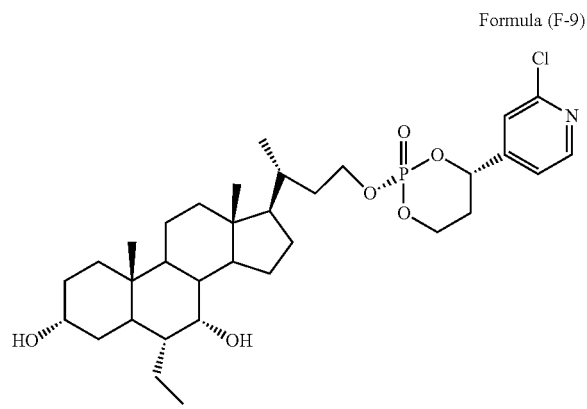
Formula (F-10)
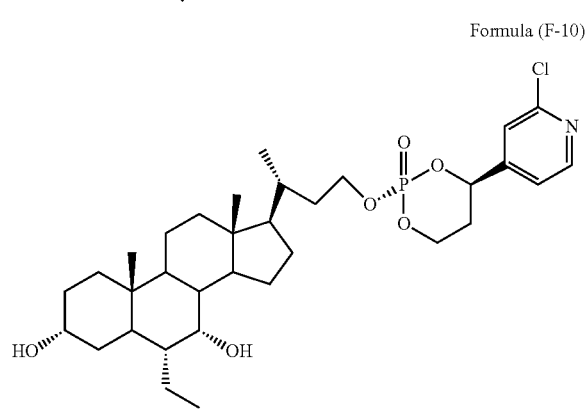
Formula (F-11)
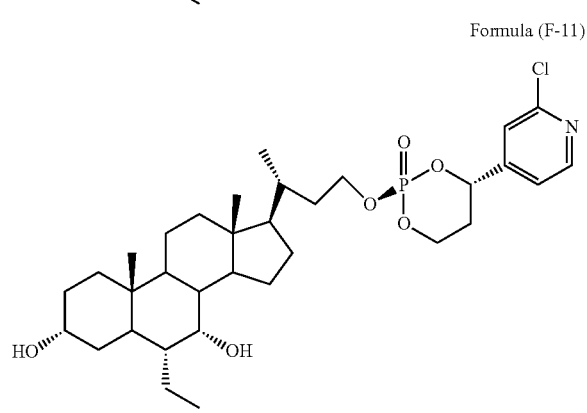
Formula (F-12)
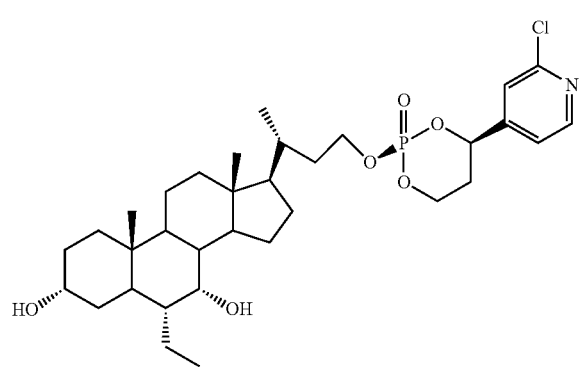
Formula (F-13)
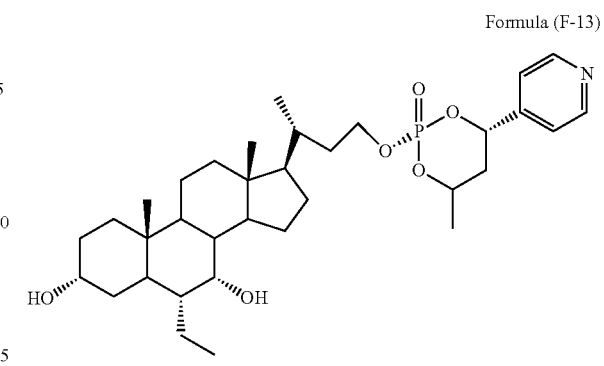
Formula (F-14)
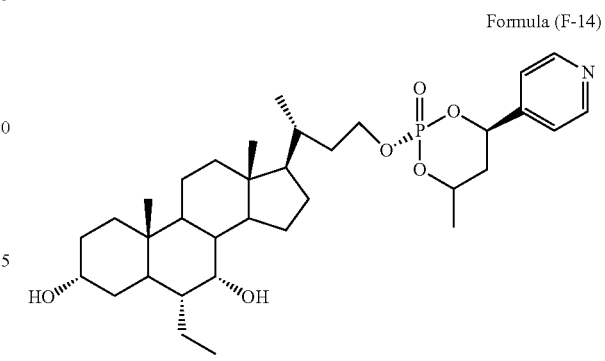
Formula (F-15)
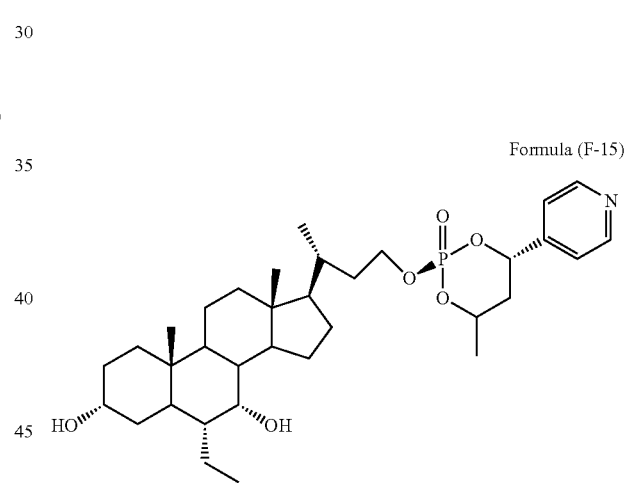
Formula (F-16)
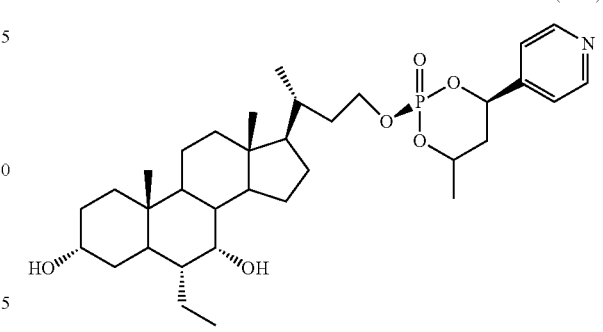

Formula (F-17)
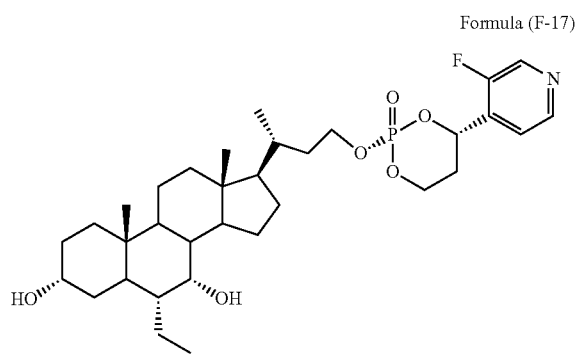
Formula (F-18)
Formula (F-19)
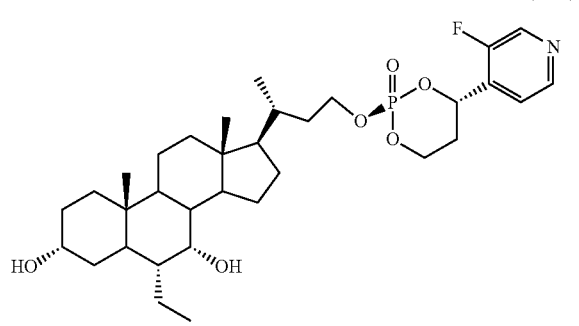
Formula (F-20)
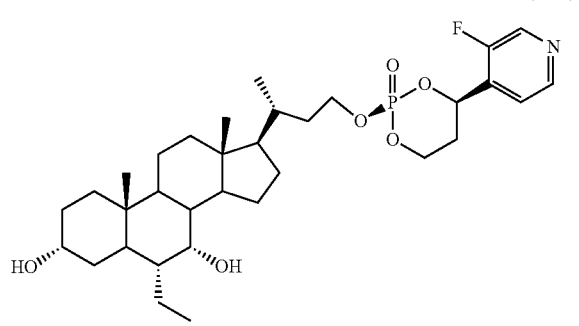
Formula (F-21)
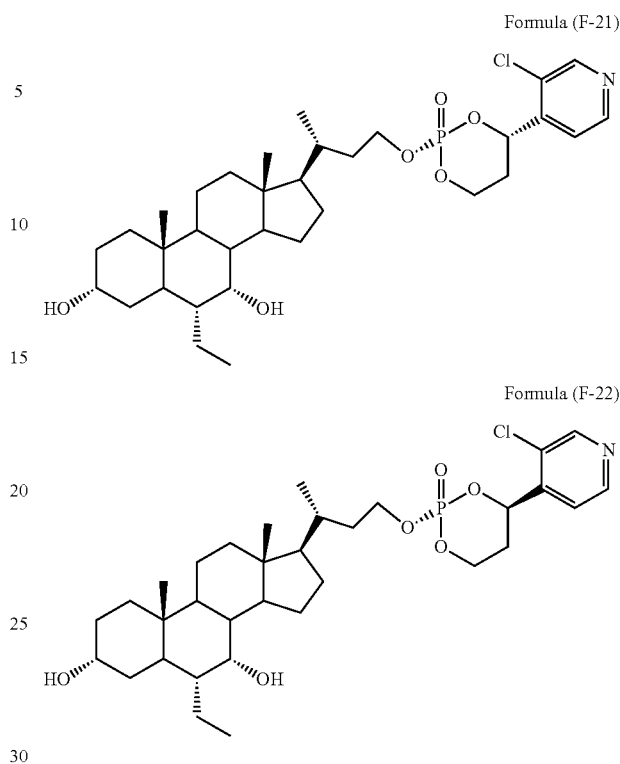
Formula (F-22)
Formula (F-23)
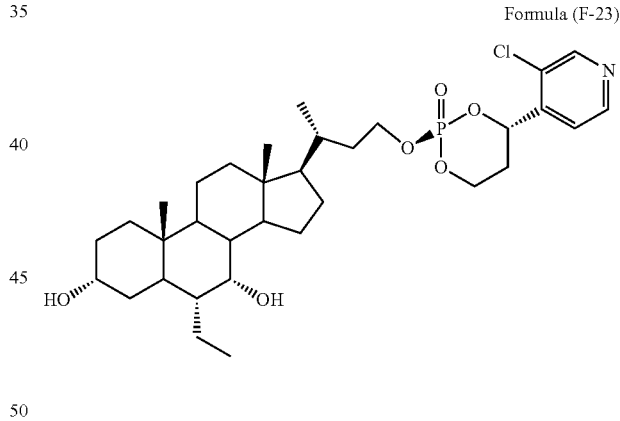
Formula (F-24)
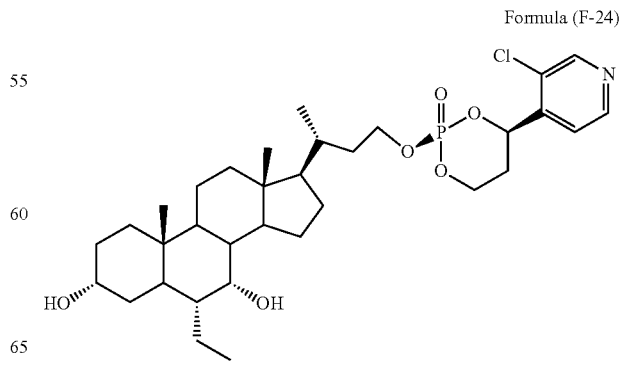

Formula (F-25)
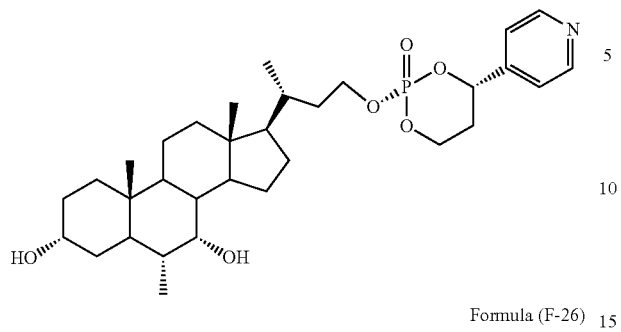

Formula (F-26)
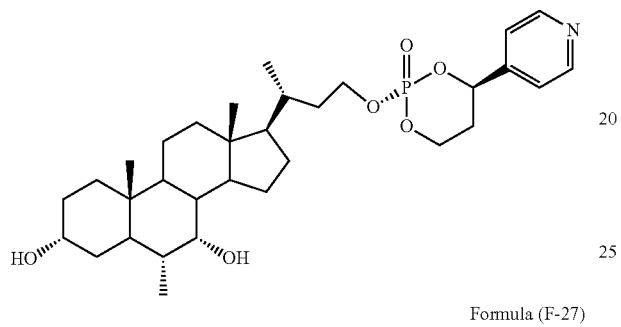

Formula (F-27)
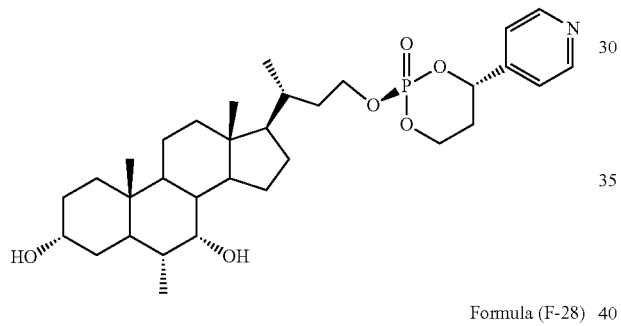

Formula (F-28)
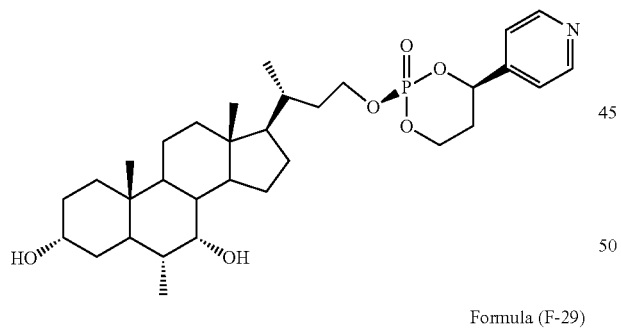

Formula (F-29)
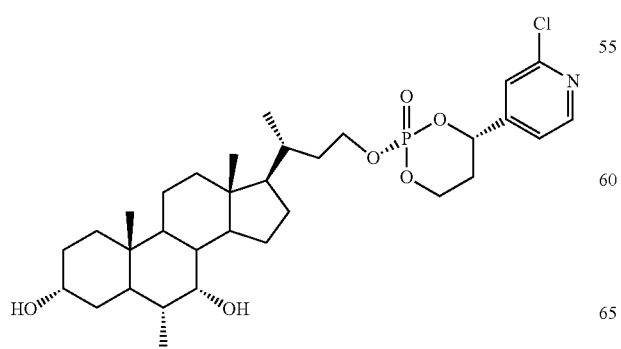

Formula (F-30)
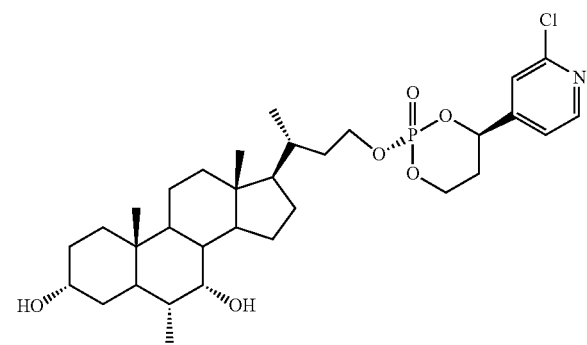

Formula (F-31)
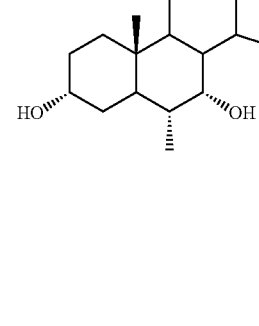

Formula (F-32)
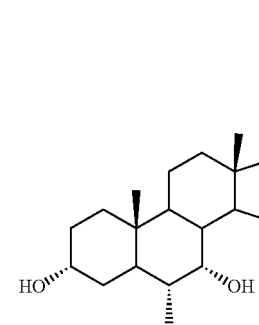

6. The salt of the bile acid derivative according to claim 1, wherein the salt of the bile acid derivative is a hydrochloride salt, mesylate salt, oxalate salt, p-toluenesulfonate salt, L-tartrate salt, fumarate salt or maleate salt of Formula (F-1), Formula (F-2), Formula (F-3), Formula (F-4), Formula (F-5), Formula (F-6), Formula (F-7), Formula (F-8), (F-9), Formula (F-10), Formula (F-11), Formula (F-12), (F-13), Formula (F-14), Formula (F-15), Formula (F-16), (F-17), Formula (F-18), Formula (F-19), Formula (F-20), (F-21), Formula (F-22), Formula (F-23), Formula (F-24), (F-25), Formula (F-26), Formula (F-27), Formula (F-28), (F-29), Formula (F-30), Formula (F-31) or Formula (F-32).

7. A method of preparing the salt of the bile acid derivative according to claim 1, comprising:

mixing and reacting a compound represented by Formula (I), a first solvent and an acid, to obtain the salt of the bile acid derivative;

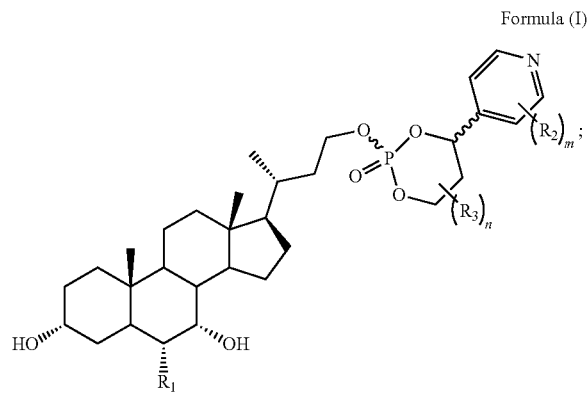

Formula (I)

wherein $R_1$ is hydrogen, substituted or unsubstituted C1-C12 alkyl or halogen;

each $R_2$ is independently one or more selected from substituted or unsubstituted C1-C12 alkyl, halogen, hydroxyl, nitro, a sulfo group and carboxyl;

m is 0, 1, 2, 3 or 4;

each $R_3$ is independently one or more selected from substituted or unsubstituted C1-C12 alkyl, halogen, hydroxyl and C6-C30 aryl;

n is 0, 1, 2, 3, 4 or 5;

the acid is an inorganic acid or an organic acid;

the inorganic acid is selected from hydrochloric acid;

the organic acid is selected from methanesulfonic acid, oxalic acid, p-toluenesulfonic acid, L-tartaric acid, fumaric acid or maleate; and the first solvent is one or more of methanol, ethanol, isopropanol, isobutanol, 2-butanone, tetrahydrofuran, dichloromethane, acetonitrile, methyl tert-butyl ether, acetone, ethyl acetate, methyl formate, isopropyl acetate or n-hexane.

8. The preparation method according to claim 7, comprising: mixing and reacting the compound represented by Formula (I), a reaction solvent and the acid; and after completion of the reaction, adding a second solvent, to obtain the salt of the bile acid derivative;

wherein the second solvent is one or more of ethyl acetate, acetonitrile, dichloromethane, methyl tert-butyl ether, acetone, methyl formate, isopropyl acetate or tetrahydrofuran;

the second solvent has a different polarity from the first solvent; and the volume ratio of the first solvent to the second solvent is 1: (1-7).

9. The salt of the bile acid derivative according to claim 1, wherein the salt of the bile acid derivative is represented by Formula (S-1), which is in the form of crystalline form A,

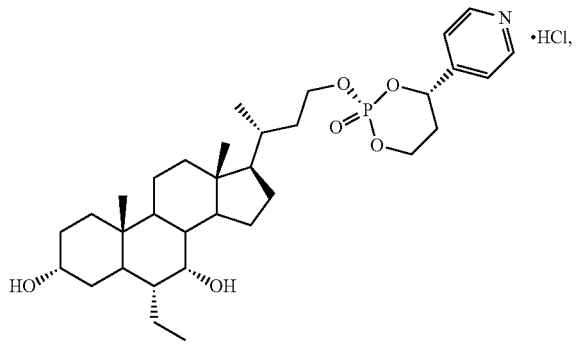

Formula (S-1)

the crystalline form A exhibits an X-ray powder diffraction spectrum comprising diffraction peaks at 2θ angles of 9.58°±0.2°, 13.79°±0.2°, 16.81°±0.2° and 19.19°±0.2°; or the crystalline form A exhibits an X-ray powder diffraction spectrum comprising diffraction peaks at 2θ angles of 6.68°±0.2°, 9.58°±0.2°, 11.37°±0.2°, 13.30°±0.2°, 13.79°±0.2°, 16.81°±0.2° and 19.19°±0.2°; or the crystalline form A exhibits a differential scanning calorimetry curve comprising an endothermic peak at 176.5° C.±3° C.; or the X-ray powder diffraction spectrum is substantially identical to FIG. 2; or the differential scanning calorimetry curve is substantially identical to FIG. 3.

10. The salt of the bile acid derivative according to claim 1, wherein the salt of the bile acid derivative is represented by Formula (S-9), which is in the form of crystalline form B,

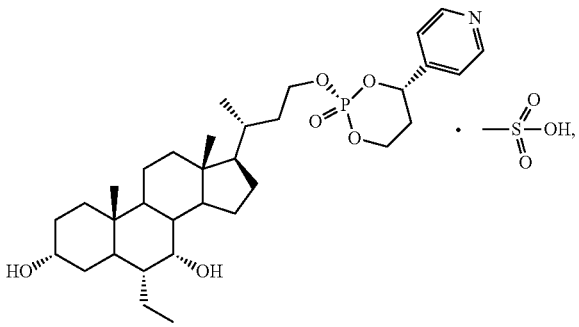

Formula (S-9)

the crystalline form B exhibits an X-ray powder diffraction spectrum comprising diffraction peaks at 2θ angles of 4.52°±0.2°, 5.20°±0.2°, 13.34°±0.2°, 13.58°±0.2° and 14.88°±0.2; or the crystalline form B exhibits an X-ray powder diffraction spectrum comprising diffraction peaks at 2θ angles of 4.52°±0.2°, 5.20°±0.2°, 7.12°±0.2°, 9.05°±0.2°, 13.34°±0.2°, 13.58°±0.2°, 14.88°±0.2°, 15.71°±0.2°, 17.48°±0.2° and 18.15°±0.2°; or the crystalline form B exhibits an X-ray powder diffraction spectrum substantially identical to FIG. 5; or the crystalline form B exhibits a differential scanning calorimetry curve and a thermogravimetric analysis curve substantially identical to FIG. 6.

11. The salt of the bile acid derivative according to claim 1, wherein the salt of the bile acid derivative is represented by Formula (S-9), which is in the form of crystalline form C,

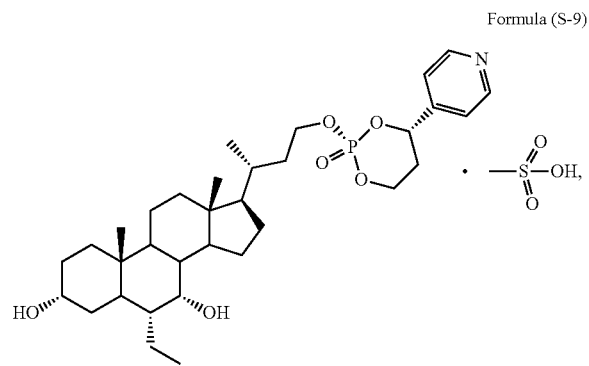

Formula (S-9)

the crystalline form C exhibits an X-ray powder diffraction spectrum comprising diffraction peaks at 2θ angles of 6.47°±0.2°, 12.04°±0.2°, 12.53°±0.2°, 13.15°±0.2° and 14.76°±0.2°; or the crystalline form C exhibits an X-ray powder diffraction spectrum comprising diffraction peaks at 2θ angles of 6.47°±0.2°, 9.19°±0.2°, 11.15°±0.2°, 11.39°±0.2°, 12.04°±0.2°, 12.53°±0.2°, 13.15°±0.2°, 14.76°±0.2°, 15.67°±0.2°, 18.48°±0.2°, 18.74°±0.2° and 20.76°±0.2°; or the crystalline form C exhibits an X-ray powder diffraction spectrum substantially identical to FIG. 7; or the crystalline form C exhibits a differential scanning calorimetry curve and a thermogravimetric analysis curve substantially identical to FIG. 8.

12. A pharmaceutical composition, comprising: the salt of the bile acid derivative according to claim 1 or the solvate thereof; and
a pharmaceutically acceptable adjuvant.

13. A method of treating or alleviating a FXR-related disease, wherein the FXR-related disease is selected from chronic liver disease, metabolic disease or portal hypertension, comprising administrating the salt of the bile acid derivative according to claim 1 or the solvate thereof to a subject in need thereof.

14. The method according to claim 13, wherein the chronic liver disease includes one or more of primary biliary cirrhosis, primary sclerosing cholangitis, liver fibrosis-related disease, drug-induced cholestasis, progressive familial intrahepatic cholestasis, cholestasis of pregnancy, alcoholic liver disease and non-alcoholic fatty liver disease;
the portal hypertension is selected from elevated portal pressure caused by liver fibrosis, hepatic sclerosis, splenomegaly or other disease; and
the metabolic disease includes hypercholesterolemia, dyslipidemia, cholesterol stone and hypertriglyceridemia.

15. A pharmaceutical composition, comprising: the crystalline form of the salt of the bile acid derivative according to claim 9, and a pharmaceutically acceptable adjuvant.

16. A pharmaceutical composition, comprising: the crystalline form of the salt of the bile acid derivative according to claim 10, and a pharmaceutically acceptable adjuvant.

17. A pharmaceutical composition, comprising: the crystalline form of the salt of the bile acid derivative according to claim 11, and a pharmaceutically acceptable adjuvant.

18. A method of treating or alleviating a FXR-related disease, wherein the FXR-related disease is selected from chronic liver disease, metabolic disease or portal hypertension, comprising administrating the crystalline form of the salt of the bile acid derivative according to claim 9 to a subject in need thereof.

19. A method of treating or alleviating a FXR-related disease, wherein the FXR-related disease is selected from chronic liver disease, metabolic disease or portal hypertension, comprising administrating the crystalline form of the salt of the bile acid derivative according to claim 10 to a subject in need thereof.

20. A method of treating or alleviating a FXR-related disease, wherein the FXR-related disease is selected from chronic liver disease, metabolic disease or portal hypertension, comprising administrating the crystalline form of the salt of the bile acid derivative according to claim 11 to a subject in need thereof.

* * * * *